US009353067B2

(12) United States Patent
Kogan et al.

(10) Patent No.: US 9,353,067 B2
(45) Date of Patent: May 31, 2016

(54) HETEROCYCLIC COMPOUNDS AND USES THEREOF IN THE TREATMENT OF SEXUAL DISORDERS

(75) Inventors: Vladimir Kogan, Rechovot (IL); Leonid Lurya, Rehovor (IL); Lev Tabachnik, Kiryat-Ono (IL)

(73) Assignee: ATIR Holding S.A., Luxembourg (LU)

( * ) Notice: Subject to any disclaimer, the term of this patent is extended or adjusted under 35 U.S.C. 154(b) by 95 days.

(21) Appl. No.: 14/110,942

(22) PCT Filed: Dec. 26, 2011
(Under 37 CFR 1.47)

(86) PCT No.: PCT/IL2011/050077
§ 371 (c)(1),
(2), (4) Date: Apr. 24, 2014

(87) PCT Pub. No.: WO2012/140642
PCT Pub. Date: Oct. 18, 2012

(65) Prior Publication Data
US 2014/0296247 A1    Oct. 2, 2014

Related U.S. Application Data

(60) Provisional application No. 61/473,773, filed on Apr. 10, 2011.

(51) Int. Cl.
*C07D 239/88* (2006.01)
*C07D 417/12* (2006.01)
*C07D 493/08* (2006.01)
*A61K 9/00* (2006.01)
*A61K 9/06* (2006.01)
*A61K 9/107* (2006.01)
*A61K 47/10* (2006.01)
*A61K 47/14* (2006.01)
*C07D 239/90* (2006.01)
*C07D 403/06* (2006.01)
*C07D 407/12* (2006.01)

(52) U.S. Cl.
CPC ............ *C07D 239/88* (2013.01); *A61K 9/0014* (2013.01); *A61K 9/06* (2013.01); *A61K 9/107* (2013.01); *A61K 47/10* (2013.01); *A61K 47/14* (2013.01); *C07D 239/90* (2013.01); *C07D 403/06* (2013.01); *C07D 407/12* (2013.01); *C07D 417/12* (2013.01); *C07D 493/08* (2013.01)

(58) Field of Classification Search
None
See application file for complete search history.

(56) References Cited

U.S. PATENT DOCUMENTS

| 3,322,756 A | 5/1967 | Ruschig et al. |
|---|---|---|
| 3,984,555 A | 10/1976 | Amschler et al. |
| 4,835,157 A | 5/1989 | Press et al. |
| 5,945,117 A | 8/1999 | El-Rashidy et al. |
| 7,151,103 B2 | 12/2006 | Borsini et al. |
| 2003/0087916 A1 | 5/2003 | Lavielle et al. |
| 2004/0048853 A1 | 3/2004 | Bergnes |
| 2004/0077667 A1 | 4/2004 | Matsuoka et al. |
| 2010/0029671 A1 | 2/2010 | Tworowski et al. |
| 2010/0216807 A1 | 8/2010 | Kogan |
| 2013/0072479 A1 | 3/2013 | Tworowski et al. |
| 2014/0107128 A1 | 4/2014 | Tworowski et al. |

FOREIGN PATENT DOCUMENTS

| EP | 0465254 | 1/1992 |
|---|---|---|
| EP | 1724267 | 11/2006 |
| WO | WO 94/07869 | 4/1994 |
| WO | WO 96/16657 | 6/1996 |
| WO | WO 98/56792 | 12/1998 |
| WO | WO 00/32590 | 6/2000 |
| WO | WO 00/50417 | 8/2000 |
| WO | WO0241894 | * 5/2002 |
| WO | WO 02/48117 | 6/2002 |
| WO | WO 2004/018058 | 3/2004 |
| WO | WO 2004/089312 | 10/2004 |
| WO | WO 2004/105700 | 12/2004 |
| WO | WO 2005/005397 | 1/2005 |
| WO | WO 2005/082887 | 9/2005 |
| WO | WO 2007/011623 | 1/2007 |
| WO | WO 2007/110868 | 10/2007 |
| WO | WO 2008/117269 | 10/2008 |
| WO | WO 2012/140642 | 10/2012 |

OTHER PUBLICATIONS

Brioni et al., Activation of dopamine D4 receptors by ABT-724 induces penile erection in rats. Proceeding of the National Academy of Sciences, 2004, 101, 6758-6763.*
Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
International Preliminary Report on Patentability Dated Feb. 16, 2009 From the International Preliminary Examining Authority Re.: Application No. PCT/IL2007/001174.

(Continued)

*Primary Examiner* — Rebecca Anderson
*Assistant Examiner* — Po-Chih Chen

(57) ABSTRACT

Biologically active compounds, which are useful for treating a sexual disorder, are provided herein. Further provided are pharmaceutical compositions formulated for transdermal composition, which comprise a biologically active compound useful for treating a sexual disorder. The compounds and pharmaceutical compositions allow for a prolonged presence of a biologically active compound in plasma. Further provided herein are methods and uses of the compounds and pharmaceutical compositions described herein in the treatment of a sexual disorder, including female sexual disorders.

20 Claims, 3 Drawing Sheets

(56) References Cited

OTHER PUBLICATIONS

Advisory Action Before the Filing of an Appeal Brief Dated Apr. 26, 2011 From the US Patent and Trademark Office Re.: U.S. Appl. No. 11/922,913.
Communication Pursuant to Article 94(3) EPC Dated Mar. 2, 2011 From the European Patent Office Re. Application No. 07827148.3.
Communication Pursuant to Article 94(3) EPC Dated Jul. 5, 2013 From the European Patent Office Re. Application No. 07827148.3.
Communication Pursuant to Article 94(3) EPC Dated Jun. 6, 2011 From the European Patent Office Re.: Application No. 07736144.2.
Communication Pursuant to Article 94(3) EPC Dated Oct. 18, 2011 From the European Patent Office Re.: Application No. 07736144.2.
Communication Pursuant to Article 94(3) EPC Dated Feb. 22, 2010 From the European Patent Office Re.: Application No. 07736144.2.
Communication Pursuant to Article 94(3) EPC Dated May 23, 2011 From the European Patent Office Re. Application No. 10153226.5.
Communication Pursuant to Article 94(3) EPC Dated Aug. 27, 2009 From the European Patent Office Re.: Application No. 07736144.2.
Communication Pursuant to Article 94(3) EPC Dated Dec. 27, 2010 From the European Patent Office Re.: Application No. 07736144.2.
Communication Relating to the Results of the Partial International Search Dated Aug. 7, 2007 From the International Searching Authority Re.: Application No. PCT/IL2007/000404.
Communication Relating to the Results of the Partial International Search Dated Mar. 19, 2008 From the International Searching Authority Re: Application No. PCT/IL2007/001174.
Communication Under Rule 71(3) EPC Dated Aug. 19, 2013 From the European Patent Office Re. Application No. 10153226.5.
Communication Under Rule 71(3) EPC Dated Jun. 22, 2012 From the European Patent Office Re. Application No. 07736144.2.
European Search Report and the European Search Opinion Dated Aug. 20, 2010 From the European Patent Office Re. Application No. 10153226.5.
International Preliminary Report on Patentability Dated Jul. 29, 2008 From the International Preliminary Examining Authority Re.: Application No. PCT/IL2007/000404.
International Search Report and the Written Opinion Dated Mar. 23, 2012 From the International Searching Authority Re. Application No. PCT/IL2011/050077.
International Search Report Dated Feb. 21, 2008 From the International Searching Authority Re.: Application No. PCT/IL2007/000404.
International Search Report Dated Oct. 29, 2008 From the International Searching Authority Re.: Application No. PCT/IL2007/001174.
Notice of Allowance Dated Aug. 13, 2013 From the US Patent and Trademark Office Re. U.S. Appl. No. 13/675,036.
Notice of Allowance Dated Jun. 22, 2012 From the US Patent and Trademark Office Re.: U.S. Appl. No. 11/922,913.
Notice of Allowance Dated Dec. 30, 2011 From the US Patent and Trademark Office Re. U.S. Appl. No. 12/532,869.
Official Action Dated Aug. 4, 2011 From the US Patent and Trademark Office Re. U.S. Appl. No. 12/532,869.
Official Action Dated Feb. 13, 2012 From the US Patent and Trademark Office Re.: U.S. Appl. No. 11/922,913.
Official Action Dated Feb. 15, 2011 From the US Patent and Trademark Office Re. U.S. Appl. No. 12/532,869.
Official Action Dated Feb. 15, 2011 From the US Patent and Trademark Office Re.: U.S. Appl. No. 11/922,913.
Official Action Dated Mar. 18, 2010 From the US Patent and Trademark Office Re.: U.S. Appl. No. 11/922,913.
Official Action Dated Aug. 25, 2011 From the US Patent and Trademark Office Re.: U.S. Appl. No. 11/922,913.
Official Action Dated Mar. 25, 2013 From the US Patent and Trademark Office Re. U.S. Appl. No. 13/675,036.
Official Action Dated Sep. 29, 2010 From the US Patent and Trademark Office Re.: U.S. Appl. No. 11/922,913.
Requisition by the Examiner Dated Jan. 23, 2013 From the Canadian Intellectual Property Office Re. Application No. 2,680,789.
Response Dated Nov. 3, 2011 to Official Action of Aug. 4, 2011 From the US Patent and Trademark Office Re. U.S. Appl. No. 12/532,869.
Response Dated Apr. 13, 2011 to Communication Pursuant to Article 94(3) EPC of Dec. 27, 2010 From the European Patent Office Re.: Application No. 07736144.2.
Response Dated Apr. 13, 2011 to Official Action of Feb. 15, 2011 From the US Patent and Trademark Office Re.: U.S. Appl. No. 11/922,913.
Response Dated Sep. 14, 2011 to Communication Pursuant to Article 94(3) EPC of May 23, 2011 From the European Patent Office Re. Application No. 10153226.5.
Response Dated May 16, 2011 to Official Action of Feb. 15, 2011 From the US Patent and Trademark Office Re. U.S. Appl. No. 12/532,869.
Response Dated Aug. 18, 2010 to Official Action of Mar. 18, 2010 From the US Patent and Trademark Office Re.: U.S. Appl. No. 11/922,913.
Response Dated Jun. 22, 2010 to Communication Pursuant to Article 94(3) EPC of Feb. 22, 2010 From the European Patent Office Re.: Application No. 07736144.2.
Response Dated Dec. 24, 2009 to Communication Pursuant to Article 94(3) EPC of Aug. 27, 2009 From the European Patent Office Re.: Application No. 07736144.2.
Response Dated Mar. 24, 2011 to European Search Report and the European Search Opinion of Aug. 20, 2010 From the European Patent Office Re. Application No. 10153226.5.
Response Dated Apr. 26, 2011 to Communication Pursuant to Article 94(3) EPC of Dec. 27, 2010 From the European Patent Office Re.: Application No. 07736144.2.
Response Dated Dec. 26, 2011 to Official Action of Aug. 25, 2011 From the US Patent and Trademark Office Re.: U.S. Appl. No. 11/922,913.
Response Dated Sep. 26, 2011 to Communication Pursuant to Article 94(3) EPC of Jun. 6, 2011 From the European Patent Office Re.: Application No. 07736144.2.
Response Dated Dec. 27, 2011 to Communication Pursuant to Article 94(3) EPC of Oct. 18, 2011 From the European Patent Office Re.: Application No. 07736144.2.
Response Dated Dec. 28, 2010 to Official Action of Sep. 29, 2010 From the US Patent and Trademark Office Re.: U.S. Appl. No. 11/922,913.
Response Dated Jun. 29, 2011 to Communication Pursuant to Article 94(3) EPC Dated Mar. 2, 2011 From the European Patent Office Re. Application No. 07827148.3.
Restriction Official Action Dated Feb. 20, 2013 From the US Patent and Trademark Office Re. U.S. Appl. No. 13/675,036.
Summons to Attend Oral Proceedings Pursuant to Rule 115(1) EPC Dated Jan. 31, 2012 From the European Patent Office Re. Application No. 07736144.2.
Written Opinion Dated Feb. 21, 2008 From the International Searching Authority Re.: Application No. PCT/IL2007/000404.
Written Opinion Dated Oct. 29, 2008 From the International Searching Authority Re.: Appliation No. PCT/IL2007/001174.
Ambinter "Ambinter Stock Screening Collection", Database Chemcats, Chemical Abstracts Service, XP-002468185, Order No. From T5926242/ON-T0518-5380/ON, Oct. 2007.
Aurora "Aurora Screening Library", Aurora Fine Chemicals, Database CHEMCATS, Chemical Abstracts Service, Order No. Kenc-0060448, XP-002468184, Sep. 2007.
Enguchard-Guciffier et al. "2-[(4-Phenylpiperazin-1-yl)Methyl]Imidazole(Di)Azines as Selective D4-Ligands. Induction of Penile Erection by 2-[4-(2-Methoxyphenyl)Piperazin-1-Ylmethyl]Imidazo[1,2-a]Pyridine (PIP3EA), A Potent and Selective D4 Partial Agonist", Journal of Medicinal Chemistry, 49: 3938-3947, 2006.
FindLaw "*Eisai Co. Ltd.* v. *Dr. Reddy's Labs., Ltd.*", FindLaw, Nos. 2007-1397, 2007-1398, Jul. 21, 2008.
Gupta et al. "Drugs Acting on the Central Nervous System. Syntheses of Substituted Quinazolones and Quinazolines and Triazepino- and Triazocinoquinazolinones", Journal of Medicinal Chemistry, XP002588388, 11(2): 392-395, 1968. p. 392: Pharmacology, Ex.26.

(56) References Cited

OTHER PUBLICATIONS

Hirose et al. "Aripiprazole, A Novel Antipsychotic Agent: Dopamine D2, Receptor Partial Agonist", The Journal of Medical Investigations, 52(Suppl.): 284-290, Nov. 2005.

Mehta et al. "Synthesis of Substuted Pyrido[3,4-b]Indole-3-Carboxamides and Related Compounds as Benzosiazepine Receptor Agonists/Antagonists", Indian Journal of Chemistry, Section B Organic Chemistry, Including Medicinal Chemistry, 27B(2): 140-143, Feb. 1988.

Testa et al. "Introduction: Metabolic Hydrolysis and Prodrug Design. Classification, Localization, and Some Physiological Roles of Hydrolytic Enzymes. The Hydrolysis of Carboxylic Acid Esters", Hydrolysis in Drug and Prodrug Metabolism, Helvetica Chimica Acta, Chap.1, 2, 7: 1-46, 370-387, 2003.

USPTO, Commerce "Examination Guidelines Update: Developments in the Obviousness Inquiry After *KSR* v. *Teleflex*", Federal Register, 75(169): 53643-53660, Sep. 1, 2010.

Requisition by the Examiner Dated Aug. 8, 2014 From the Canadian Intellectual Property Office Re. Application No. 2,680,789.

Official Action Dated Sep. 17, 2014 From the US Patent and Trademark Office Re. U.S. Appl. No. 14/108,371.

Requisition by the Examiner Dated Oct. 23, 2013 From the Canadian Intellectual Property Office Re. Application No. 2,680,789.

International Preliminary Report on Patentability Dated Oct. 24, 2013 From the International Preliminary Examining Authority Re. Application No. PCT/IL2011/050077.

Communication Pursuant to Article 94(3) EPC Dated Aug. 26, 2014 From the European Patent Office Re. Application No. 07827148.3.

Restriction Official Action Dated May 27, 2014 From the US Patent and Trademark Office Re. U.S. Appl. No. 14/108,371.

European Search Report Dated May 6, 2015 From the European Patent Office Re. Application No. 15150907.2.

\* cited by examiner

HETEROCYCLIC COMPOUNDS AND USES THEREOF IN THE TREATMENT OF SEXUAL DISORDERS

RELATED APPLICATIONS

This application is a National Phase of PCT Patent Application No. PCT/IL2011/050077 having International filing date of Dec. 26, 2011, which claims the benefit of priority under 35 USC §119(e) of U.S. Provisional Patent Application No. 61/473,773 filed on Apr. 10, 2011.

FIELD AND BACKGROUND OF THE INVENTION

The present invention, in some embodiments thereof, relates to the field of pharmacology and, more particularly, but not exclusively, to heterocyclic compounds and their use in the treatment of sexual disorders such as decreased libido, orgasm disorder and erectile dysfunction. The present invention, in some embodiments thereof, relates to novel heterocyclic compounds, to heterocyclic compounds which exhibit substantial activity in treating sexual disorders in female, and/or to novel regimens for treating sexual disorders while utilizing the described heterocyclic compounds.

Selective inhibitors of PDE5 (phosphodiesterase-5) are used for inducing penile erection by raising cGMP levels (Terret et al., 1996). PDE5 hydrolyses cGMP (cyclic guanosine monophosphate), and is located prominently in the penis. Inhibition of PDE5 results in higher cGMP levels in the penis. The cGMP mediates erection by inducing relaxation of the arterial smooth muscle, thereby increasing the volume of blood flowing through the arteries. The increased volume of blood entering the penis leads to an erection.

Male patients suffering from erectile dysfunction generally respond well to medications of the PDE5 inhibitor family, with approximately 80% success rates (Evans et al., 1980; Hyttel, 1982). The principal currently available drugs belonging to the PDE5 inhibitor family are tadalafil (Cialis™), vardenafil (Levitra™) and sildenafil (Viagra™) the most famous one being Viagra™ (sildenafil).

While sildenafil is considered a selective inhibitor of PDE5, it has long been recognized that it effects on other body organs and hence its use is associated with several adverse side effects such as nausea, headache, and cutaneous flushing. These clinically significant adverse effects are thought to be due to nonspecific inhibition of other PDEs exhibited by this compound (Beavo, 1998; Moreland and Goldstein, 1995).

Although clitoral erection in women is caused by an analogous mechanism to that of penile erection, PDE5 inhibitors have had little success in treating sexual dysfunction in women.

In addition to PDE5, experimental data indicate that several neurotransmitters and neuropeptides in the central nervous system are involved in the control of penile erection and sexual behavior, one such prominent neurotransmitter being dopamine (Melis and Argiolas, 1995; Andersson, 2001). In contrast to PDE5 inhibition, which directly affects the blood vessels in the penis, dopamine is involved in the regulation of penile activity by the central nervous system.

Dopamine is one of the key mediators in the CNS and is involved in a variety of physiological functions, including sexual behavior, cognition, motor coordination, cardiovascular control, reward and hormonal regulation. It has been shown that several dopamine receptor agonists such as apomorphine, quinpirole, quinelorane, PIP3EA, and (−)-3-(3-hydroxyphenyl)-N-n-propylpiperidine (3-PPP) induce penile erection after systemic administration in mammals (Melis and Argiolas, 1995; Enguehard-Gueffier et al. 2006).

Apomorphine induces erection by activating the D4 receptor, although other dopamine receptors may also be involved (Brioni et al., 2004). U.S. Pat. No. 5,945,117 describes amelioration of female sexual dysfunction by sublingual administration of apomorphine.

However, apomorphine is classified as a nonselective agonist because it activates all of the dopamine receptor subtypes (Missale, 1998). It is believed that such non-selectivity is associated with the known emetic action that substantially restricts the practical application of apomorphine.

ABT-724 (2-[(4-pyridin-2-ylpiperazin-1-yl)methyl]-1H-benzimidazole) is a selective D4 agonist (Brioni et al., 2004). Methods of using ABT-724 and related compounds in the treatment of various sexual dysfunctions are disclosed in U.S. Pat. Nos. 7,022,728 and 6,960,589, to Cowart et al.

PIP3EA is a selective D4 agonist, and induces penile erection via D4 activation (Enguehard-Gueffier et al. 2006).

Other highly selective dopamine receptor D4 agonists have also been developed. These include, for example, PD-168077 (Melis et al., 2006), A-412997 (Moreland et al., 2005) and A-381393 (Nakane et al., 2005).

U.S. Pat. No. 7,115,103 describes the use of flibanserin, which binds to serotonin receptors, for treating disorders of sexual desire.

International Patent Application PCT/IL2007/000404 (published as WO 2007/110868) describe heterocyclic compounds which exhibit a dopamine receptor (e.g., D4 receptor) agonist activity and/or a PDE5 inhibitory activity, for use in the treatment of sexual disorders such as decreased libido, orgasm disorder and erectile dysfunction.

SUMMARY OF THE INVENTION

According to an aspect of some embodiments of the present invention, there is provided a compound having the general Formula I:

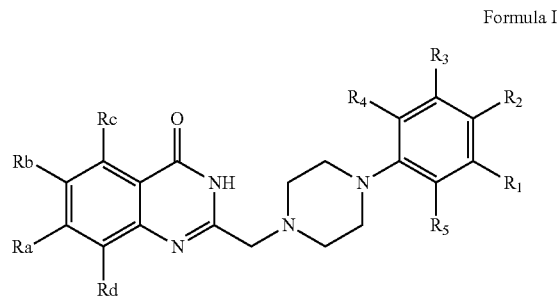

Formula I or a pharmaceutically acceptable salt thereof,
wherein:

Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, wherein at least one of $R_1$-$R_5$ has the general Formula II:

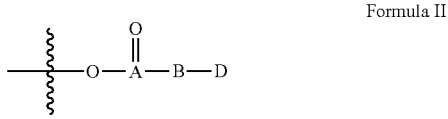

Formula II wherein:

A is selected from the group consisting of a carbon atom and S=O;

B is absent or is a substituted or non-substituted, saturated or non-saturated alkylene chain; and D is selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted.

According to an aspect of some embodiments of the present invention, there is provided a pharmaceutical composition comprising a compound described herein and a pharmaceutically acceptable carrier.

According to an aspect of some embodiments of the present invention, there is provided a method of treating a sexual disorder, the method comprising administering to a subject in need thereof a therapeutically effective amount of a compound described herein.

According to an aspect of some embodiments of the present invention, there is provided a pharmaceutical composition comprising a compound having the general Formula III:

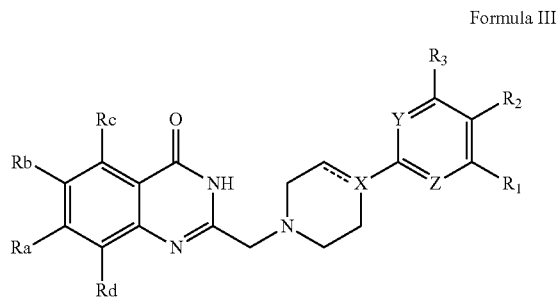

Formula III or a pharmaceutically acceptable salt thereof,
wherein:
the dashed line denotes a saturated or non-saturated bond;
X is selected from the group consisting of CH, C and N, such that when X is C the dashed line denotes a non-saturated bond and when X is CH or N the dashed line denotes a saturated bond;
Y is N or $CR_4$;
Z is N or $CR_5$; and
Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, and a pharmaceutically acceptable carrier,
the composition being formulated for transdermal administration.

According to an aspect of some embodiments of the present invention, there is provided a method of treating a sexual disorder, the method comprising transdermally administering to a subject in need thereof a therapeutically effective amount of a pharmaceutical composition described herein.

According to an aspect of some embodiments of the present invention, there is provided a method of treating a sexual disorder in a female subject in need thereof, the method comprising administering to the female subject a therapeutically effective amount of a compound of the general Formula:

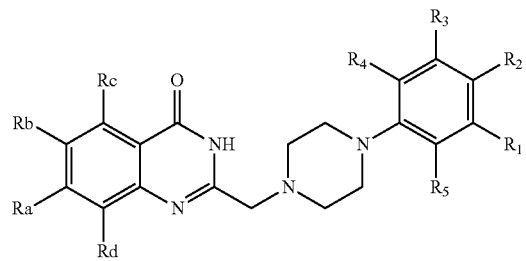

or a pharmaceutically acceptable salt thereof,
wherein:
Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted,
wherein at least one of $R_1$-$R_5$ is selected from the group consisting of hydroxy and a moiety having the general Formula:

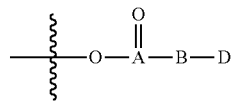

wherein:
A is selected from the group consisting of C and S=O;
B is absent or is a substituted or non-substituted, saturated or non-saturated alkylene chain; and
D is selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted,
thereby treating the sexual disorder in the female subject.

According to an aspect of some embodiments of the present invention, there is provided a use of a compound of the general Formula:

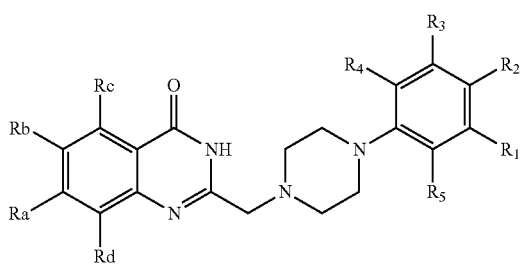

or a pharmaceutically acceptable salt thereof,
wherein:
Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, wherein at least one of $R_1$-$R_5$ is selected from the group consisting of hydroxy and a moiety having the general Formula:

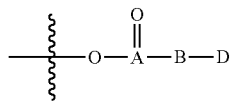

wherein:
A is selected from the group consisting of C and S=O;
B is absent or is a substituted or non-substituted, saturated or non-saturated alkylene chain; and
D is selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, in the manufacture of a medicament for treating a sexual disorder in a female subject.

According to an aspect of some embodiments of the present invention, there is provided a pharmaceutical composition comprising a compound of the general Formula:

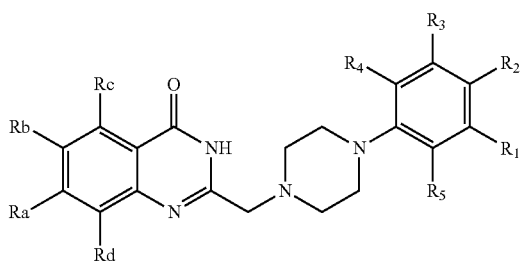

or a pharmaceutically acceptable salt thereof,
wherein:
Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, wherein at least one of $R_1$-$R_5$ is selected from the group consisting of hydroxy and a moiety having the general Formula:

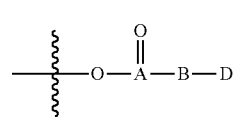

wherein:
A is selected from the group consisting of C and S=O;
B is absent or is a substituted or non-substituted, saturated or non-saturated alkylene chain; and
D is selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, and a pharmaceutically acceptable carrier,
for use in the treatment of a sexual disorder in a female subject.

According to some embodiments of the invention, A is a carbon atom.

According to some embodiments of the invention, D is a substituted or non-substituted aryl.

According to some embodiments of the invention, the aryl is phenyl.

According to some embodiments of the invention, the aryl is substituted by at least one substituent selected from the group consisting of alkyl, alkoxy, aryloxy, hydroxy, amine, nitrile, nitro, and halide.

According to some embodiments of the invention, D is a cycloalkyl selected from the group consisting of cyclopropyl, cyclopentyl, cyclohexyl, adamantyl, and 3-oxo-4,7,7-trimethyl-2-oxa-bicyclo[2.2.1]heptanyl.

According to some embodiments of the invention, D is a non-substituted alkyl.

According to some embodiments of the invention, B is absent.

According to some embodiments of the invention, B is alkyl.

According to some embodiments of the invention, the compound is characterized by a half-life in a range of from 30 minutes to 8 hours in human plasma at 37° C.

According to some embodiments of the invention, the compound is devoid of PARP-1 inhibitory activity.

According to some embodiments of the invention, the compound is for use in the treatment of a sexual disorder in a subject in need thereof.

According to some embodiments of the invention, the pharmaceutical composition is packaged in a packaging material and identified in print, in or on the packaging material, for use in the treatment of a sexual disorder in a subject in need thereof.

According to some embodiments of the invention, the pharmaceutical composition is formulated for transdermal administration.

According to some embodiments of the invention, the compound forms a part of a pharmaceutical composition formulated for transdermal administration.

According to some embodiments of the invention, the medicament is formulated for transdermal administration.

According to some embodiments of the invention, the compound is administered transdermally.

According to some embodiments of the invention, the subject is a female subject.

According to some embodiments of the invention, the sexual disorder is selected from the group consisting of decreased libido, female sexual arousal disorder, and orgasm disorder.

According to some embodiments of the invention, the sexual disorder is selected from the group consisting of decreased libido, female sexual arousal disorder, erectile dysfunction, and orgasm disorder.

According to some embodiments of the invention, at least one of $R_1$-$R_5$ is hydroxy.

According to some embodiments of the invention, $R_1$ is hydroxy.

According to some embodiments of the invention, $R_1$ is selected from the group consisting of hydroxy and the moiety having the general Formula:

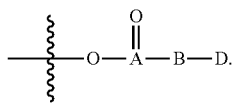

According to some embodiments of the invention, at least one of $R_1$-$R_5$ is the moiety having the general Formula:

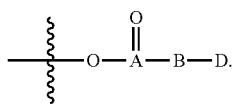

According to some embodiments of the invention, at least one of $R_1$-$R_5$ is selected from the group consisting of carboxy and sulfonate having the general Formula II:

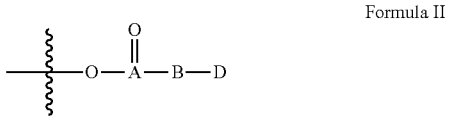

Formula II wherein:

A is selected from the group consisting of a carbon atom and S=O;

B is absent or is a substituted or non-substituted, saturated or non-saturated alkylene chain; and D is selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted.

According to some embodiments of the invention, $R_1$ has the general Formula II.

According to some embodiments of the invention, X is N.

According to some embodiments of the invention, Y is $CR_4$ and Z is $CR_5$.

According to some embodiments of the invention, Ra, Rc, and Rd are each hydrogen.

According to some embodiments of the invention, Rb is selected from the group consisting of hydrogen and halide.

According to some embodiments of the invention, a concentration of the compound in the pharmaceutical composition is at least 10 mg per 1 gram of the carrier.

According to some embodiments of the invention, the pharmaceutical composition is in a form of an oil-in-water emulsion.

According to some embodiments of the invention, a lipophilic phase of the emulsion comprises at least one solvent selected from the group consisting of propylene glycol, propylene glycol monolaurate, and propylene glycol laurate.

According to some embodiments of the invention, the lipophilic phase further comprises at least one solubilizing agent.

According to some embodiments of the invention, the solubilizing agent is selected from the group consisting of lauroyl macrogolglycerides.

According to some embodiments of the invention, the pharmaceutical composition further comprises at least one surfactant.

According to some embodiments of the invention, the surfactant is selected from the group consisting of phosphatidyl choline and caprylocapryl macrogolglyceride.

According to some embodiments of the invention, the pharmaceutical further comprises at least one sustained-release agent.

According to some embodiments of the invention, an aqueous phase of the emulsion comprises carboxymethyl cellulose.

According to some embodiments of the invention, the emulsion comprises from 60 to 97.5 weight percents of a lipophilic phase.

According to some embodiments of the invention, the lipophilic phase comprises propylene glycol, Lauroglycol 90, Gelucire® 44/14, phosphatidyl choline, Labrasol®, and Gelucire® 50/13.

According to some embodiments of the invention, the lipophilic phase comprises:
  from 25 to 75 weight percents propylene glycol;
  from 8 to 30 weight percents Gelucire® 44/14;
  from 1 to 4 weight percents Labrasol®;
  from 1 to 4 weight percents Lauroglycol 90;
  from 2.5 to 10 weight percents Gelucire® 50/13;
  from 3 to 12 weight percents phosphatidyl choline; and
  from 0 to 1 weight percent vitamin E TPGS.

According to some embodiments of the invention, the pharmaceutical composition is stable for at least 2 weeks at room temperature.

According to some embodiments of the invention, the pharmaceutical composition is characterized by an ability to release the compound for at least two hours upon administration on a skin of a subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A and 1B show results from two independent assays);

FIGS. 1A and 1B show results from two independent assays); FIGS. 1A and 1B show results from two independent assays).

DESCRIPTION OF SPECIFIC EMBODIMENTS OF THE INVENTION

Figure 1A:
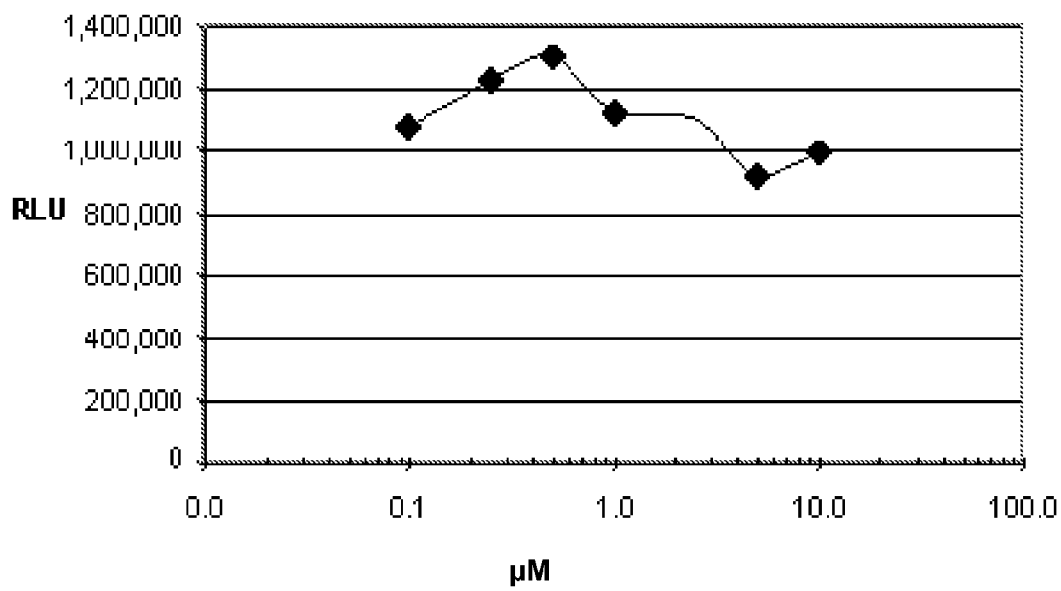
FIGS. 1A and 1B are graphs showing the activity of PARP in the presence of various concentrations of R-55 (PARP activity is represented as relative light units (RLU)

The present invention, in some embodiments thereof, relates to the field of pharmacology and, more particularly, but not exclusively, to heterocyclic compounds and their use in the treatment of sexual disorders such as decreased libido, orgasm disorder and erectile dysfunction. The present invention, in some embodiments thereof, relates to novel heterocyclic compounds, to heterocyclic compounds which exhibit substantial activity in treating sexual disorders in female, and/or to novel regimens for treating sexual disorders while utilizing heterocyclic compounds.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, growing evidence suggests that D4 dopamine receptor agonists may also have a role in the treatment and/or prevention of erectile dysfunction, as well as other sexual disorders (including female sexual disorders), such as orgasm disorder and sexual desire disorder.

However, as further discussed hereinabove, current treatment methods are severely limited by side effects such as emesis in the case of the non-selective dopamine receptor agonist apomorphine.

While conceiving the present invention, it was envisioned that a novel and effective treatment of sexual disorders could be achieved by the design and preparation of selective D4 dopamine receptor agonists which exhibit a specificity and pharmacokinetic profile suitable for use as a relatively long-lasting therapeutic agent.

As described hereinabove, International Patent Application PCT/IL2007/000404 (published as WO 2007/110868) describes heterocyclic D4 receptor agonists.

While investigating the compounds described in International Patent Application PCT/IL2007/000404, the present inventors sought methods for improving the agonist activity thereof and providing for a longer lasting activity.

While reducing the present invention to practice, a plurality of novel heterocyclic compounds were designed to provide longer lasting plasma concentrations of an active therapeutic agent. The disclosed novel compounds feature an esterified substituent at a certain position of the heterocyclic compound, which provides for the improved pharmacological performance. Representative examples of such compounds are presented in Examples 2 and 3 in the Examples section that follows, and the improved performance thereof is demonstrated in Example 4 in the Examples section that follows. As is demonstrated in Example 4, the esterified compounds were found highly efficacious in providing a long lasting plasma concentration of a therapeutic agent capable of selectively activating the D4 dopamine receptor.

While further reducing the present invention to practice, transdermal formulations of previously described heterocyclic compounds were designed and have been surprisingly found to provide longer lasting plasma concentrations of the active therapeutic agent. Representative examples of transdermal formulations are presented in Example 5 in the Examples section that follows and the improved performance thereof is demonstrated in Example 6 in the Examples section that follows. As is demonstrated in Example 6, the transdermal formulations were found highly efficacious in providing a long lasting plasma concentration of a therapeutic agent capable of selectively activating the D4 dopamine receptor.

In addition, representative examples of particularly effective and selective active therapeutic agents were identified (see Examples 7 and 8).

Hence, according to an aspect of the present invention there is provided a compound having the general formula I:

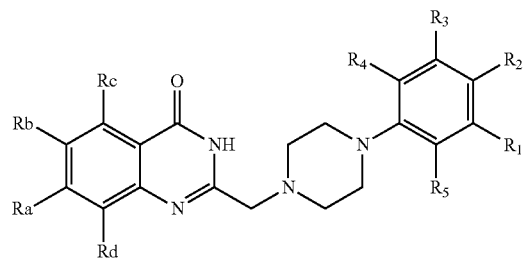

Formula I or a pharmaceutically acceptable salt thereof, wherein Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, wherein at least one of $R_1$-$R_5$ (and optionally only one of $R_1$-$R_5$) is an ester moiety having the general Formula II:

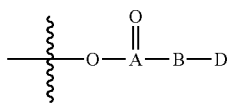

Formula II wherein:

A is selected from the group consisting of a carbon atom and S=O;

B is absent or is a substituted or non-substituted, saturated or non-saturated alkylene chain; and D is selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted.

Each of the compounds according to these embodiments of the present invention thus comprises an ester moiety as one of the $R_1$-$R_5$ substituents in Formula I hereinabove. These compounds are therefore referred to herein also as "esterified compounds".

Without being bound by any particular theory, it is believed that the ester moiety of the esterified compound undergoes gradual hydrolysis in vivo, to release an active compound comprising a hydroxy group in place of the ester moiety. It is further believed that the active compound comprising a hydroxy group, while being therapeutically effective in vivo, is limited by a relatively low availability in plasma following oral administration, and that the esterified compound provides a considerably higher availability (e.g., oral bioavailability) in plasma.

Hence, the variables Ra-Rd and $R_1$-$R_5$ are optionally selected such that a compound produced by hydrolysis of an above-described ester moiety is present in vivo (e.g., in plasma) at a therapeutically effective concentration, following oral administration of the esterified compound.

As further shown in Examples section, compounds having a hydroxy group at the $R_1$ position (i.e., at a meta position with respect to the piperazine moiety) are particularly effective (e.g., as selective D4 dopamine receptor agonists).

Hence, according to some embodiments, at least $R_1$ is an ester moiety described herein. Thus, hydrolysis of an ester bond results in a hydroxyl group at the $R_1$ position.

As further shown in the Examples section, exemplary compounds according to embodiments of the invention do not exhibit PARP (poly(ADP-ribose)polymerase) inhibitory activity, in contrast to some quinazolinone derivatives, particularly derivatives comprising quinazolinone linked via a three-carbon moiety (e.g., trimethylene) to substituted pyridinyl and piperazinyl moieties, which have been identified as potent PARP inhibitors [U.S. Patent Application Publication No. 2004/0077667; Iwashita et al., FEBS Lett 579:1389-1393(2005); Hattori et al., J Med Chem 47:4151-4154 (2004)]. PARP plays a natural role in repair of DNA damage, and inhibition of PARP may lead to undesirable side effects in any treatment of a sexual disorder.

Hence, according to some embodiments, the active compound described herein is devoid of PARP-1 inhibitory activity. In some embodiments, the active compound described herein is devoid of PARP inhibitory activity.

Herein, the phrase "devoid of PARP-1 inhibitory activity" means that the active compound does not reduce PARP-1 activity by more than 30% at concentrations of 10 μM of the active compound or less. Optionally, the active compound does not reduce PARP-1 activity by more than 25%, and optionally not more than 20%.

Herein, the phrase "devoid of PARP inhibitory activity" means that the active compound does not reduce activity of any type of PARP by more than 30% at concentrations of 10 μM of the active compound or less. Optionally, the active compound does not reduce a PARP activity by more than 25%, and optionally not more than 20%.

PARP activity (e.g., PARP-1 activity) may be assayed by any suitable technique used in the art (e.g., according to assay procedures exemplified herein).

Without being bound by any particular theory, it is believed that the methylene bridge of compounds described herein results in significantly less PARP inhibitory activity than is obtained for PARP inhibitors having a three-carbon (e.g., trimethylene) bridge, as a methylene bridge results in a different molecular geometry and a reduced molecular flexibility, in comparison to a three-carbon bridge.

Acids and acyl chlorides for preparing exemplary ester moieties according to some embodiments of the invention are described in the Examples section below. The structures of the exemplary ester moieties will be readily apparent to one of skill in the art in view of the corresponding carboxylic acid and/or acyl chloride.

As exemplified in the Examples below, the rate of release of the active therapeutic agent (e.g., by hydrolysis of the esterified compound) can be controlled by selection of an appropriate ester moiety. Thus, for example, carboxy esters comprising small unsubstituted moieties (e.g., alkyl, cycloalkyl, aryl or heteroaryl) resulted in relatively rapid hydrolysis (e.g., wherein $T_{1/2}$ in human plasma is about 150 minutes or less), whereas sulfonate ester moieties resulted in relatively slow hydrolysis (e.g., wherein the half-life ($T_{1/2}$) in human plasma is over 1000 minutes or less).

Thus, the half-life in human plasma may optionally be manipulated as desired by selecting a carboxy ester (for shorter half-lives) or a sulfonate ester (for longer half-lives).

Thus, in some embodiments, the ester is a sulfonate ester, for example, an alkyl-substituted sulfonate ester or an aryl-substituted sulfonate ester. Methanesulfonate is an exemplary alkyl-substituted sulfonate ester moiety and p-toluene-sulfonate is an exemplary aryl-substituted ester moiety.

In some embodiments, the ester moiety is carboxy (i.e. A is a carbon atom) rather than sulfonate (wherein A is S=O).

For many applications in treating a sexual disorder, a very long (e.g., >1000 minutes) $T_{1/2}$ in plasma (e.g., as is typical of sulfonate esters) is unnecessary, as administration of a compound may be effected as needed (e.g., prior to sexual activity).

Thus, in some embodiments the esterified compound is characterized by a $T_{1/2}$ less than 1000 minutes in human plasma at 37° C. In some embodiments, the esterified compound is characterized by a $T_{1/2}$ in a range of from 30 minutes to 8 hours in human plasma at 37° C. Optionally, the $T_{1/2}$ is at least 1 hour and optionally at least 2 hours. Optionally, the $T_{1/2}$ is 6 hours or less, and optionally 4 hours or less.

As exemplified herein, propionate esters (wherein B is absent and D is ethyl) exhibit relatively rapid hydrolysis (e.g., wherein $T_{1/2}$ is approximately 10 minutes in human plasma).

Hence, according to some embodiments, the ester moiety is terminated by a moiety (represented by variable D) which is relatively bulky, i.e., wherein D comprises at least 3 carbon atoms and/or heteroatoms, optionally at least 4, and optionally at least 5 carbon atoms and/or heteroatoms. In some embodiments, the bulky moiety is a non-linear group, comprising for example, a branched moiety (e.g., branched alkyl, alkenyl or alkynyl) and/or a cyclic moiety.

In some embodiments, the bulky moiety (represented by variable D) is a cyclic moiety selected from the group consisting of cycloalkyl, heteroalicyclic, aryl and heteroaryl, each being substituted or non-substituted.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthyl and anthracenyl. Phenyl and naphthyl are exemplary aryl groups. The aryl group may be substituted or non-substituted. Exemplary non-substituted aryl groups include non-substituted phenyl and naphthyl.

When an aryl is substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, nitrile, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Exemplary substituents include alkyl (particularly methyl), nitro, hydroxy, alkoxy (particularly methoxy), aryloxy (particularly phenoxy), nitrile, amino, and halo.

Exemplary substituted aryls include substituted phenyls, such as 2-methylphenyl, 2-nitrophenyl, 2-hydroxyphenyl, 2-methoxyphenyl, 2-phenoxyphenyl, 3-nitrophenyl, 3-cyanophenyl, 3-aminophenyl, 4-methoxyphenyl, 4-ethoxyphenyl, 4-propylphenyl, 4-methylphenyl, 4-chlorophenyl, 4-bromophenyl, 4-fluorophenyl, 5-hydroxy-2-aminophenyl, 3-methyl-2-hydroxyphenyl, 4-methyl-2-hydroxyphenyl, 5-methyl-2-hydroxyphenyl, 3-isopropyl-2-hydroxyphenyl, 3,4-diaminophenyl, 4-amino-2,3,5,6-tetrafluorophenyl, 2,3,4,5,6-pentafluorophenyl, and fluoren-1-yl.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazine, pyrazole, pyridine, pyrimidine, benzopyrone (e.g., 4-oxo-1-benzopyran), quinoline, isoquinoline and purine. Pyrrole, thiazole, pyrazine and 4-oxo-1-benzopyran are exemplary heteroaryl groups. The heteroaryl group may be substituted or non-substituted. Pyrrol-2-yl and 1,3-thiazol-2-yl are exemplary non-substituted heteroaryl groups.

When a heteroaryl is substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, nitrile, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. It is to be appreciated that a substituent (e.g., oxo) may be a component of the conjugated pi-electron system. Alkyl (particularly methyl), oxo and amino are exemplary substituents. Exemplary substituted heteroaryl groups include 4-oxo-1-benzopyran-2-yl, 5-methyl-pyrazin-2-yl, and 3-amino-pyrazin-2-yl.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropyl, cyclobutyl, cyclopentyl, cyclopentenyl, cyclohexyl, cyclohexadiene, cycloheptyl, cycloheptatrienyl, norbornyl (i.e., bicyclo[2.2.1]heptanyl) and adamantyl. Exemplary cycloalkyl groups include cyclopropyl, cyclobutyl, cyclohexyl, norbornyl and adamantyl. A cycloalkyl group may be substituted or non-substituted. Exemplary non-substituted cycloalkyl groups include cyclopropyl, cyclopentyl, cyclohexyl, and adamantyl.

When a cycloalkyl is substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, nitrile, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Oxo and methyl are exemplary substituents. Camphanyl(3-oxo-4,7,7-trimethyl-2-oxa-bicyclo[2.2.1]heptanyl) is an exemplary substituted cycloalkyl group.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, nitrile, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Representative examples are piperidine, piperazine, tetrahydrofuran, tetrahydropyran, morpholine and the like. Tetrahydrofuran-2-yl is an exemplary heteroalicyclic group.

As exemplified in the Examples section below, ester moieties comprising aryl and heteroaryl tend to exhibit an advantageous half-life in human plasma (e.g., in a range of from 2 to 8 hours), wherein the half-life depends on whether a substituent is present, and on the nature (e.g., size) of the substituent, if present.

For example, as exemplified in the Examples section below, compounds comprising a non-substituted aryl (e.g., phenyl) or heteroaryl (e.g., pyrrol-2-yl) moiety exhibit a half-life in human plasma of at least about 2 hours, whereas compounds comprising non-substituted cycloalkyl (e.g., cyclohexyl) exhibit a considerably shorter half-life.

In some embodiments, a substituent of an aryl or heteroaryl is selected from the group consisting of alkyl, alkoxy, aryloxy, hydroxy, amine, nitrile, nitro and halide. In some embodiments, an aryl group is substituted with the aforementioned substituent(s).

As further exemplified below, ring substituents (e.g., phenyl substituents) slow hydrolysis considerably, to a degree which is correlated to the size of the substituent.

According to optional embodiments, the substituent is small, for example, 1 or 2 atoms in size (excluding hydrogen atoms). Examples of such substituents include methyl, ethyl, methoxy, hydroxy, amino (—NH$_2$), nitrile and halide (fluoro or chloro, in some embodiments). As exemplified below, small substituents lengthen the half-life of the esterified compound to a significant, but not excessive extent. Thus, for example, compounds having such substituents of 1 or 2 atoms tend to have half-lives in human plasma of up to about 8 hours (480 minutes), whereas larger substituents (e.g., ethoxy) may have considerably longer half-lives (e.g., >1000 minutes).

The aryl, heteroaryl, heteroalicyclic or cycloalkyl may optionally be attached directly to A, wherein B is absent (e.g., such that the ester moiety is benzoyl or a derivative thereof).

Alternatively, the aryl, heteroaryl or cycloalkyl is attached via a saturated or unsaturated alkylene chain represented by the variable B (e.g., such that the ester moiety is phenylacetyl or a derivative thereof).

It is to be appreciated that, as exemplified below, such alkylene chains do not exhibit a tendency to slow hydrolysis, in contrast with other substituents, as described herein.

As used herein, an "alkylene chain" refers to a bi-radical moiety (i.e., a divalent radical) comprising 1-20 carbon atoms covalently linked to one another by single, double or triple bonds. In a "saturated" alkylene chain, the carbon atoms are linked to one another solely by single bonds, whereas an "unsaturated" alkylene chain comprises at least one double bond and/or triple bond between carbon atoms. The alkylene chain is optionally substituted by one or more substituents, whereby the substituents can be, for example, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, nitrile, nitro, azide, phosphonyl, phosphinyl, oxo, carbonyl, thiocarbonyl, urea, thiourea, carbamyl, N-carbamyl, O-thiocarbamyl, N-thiocarbamyl, C-amido, N-amido, C-carboxy, O-carboxy, sulfonamido, and amino, as these terms are defined herein. Optionally, B is an alkylene chain of up to 10 carbon atoms, optionally of up to 4 carbon atoms (e.g., a saturated alkylene of 1 to 4 carbon atoms), and optionally 1 or 2 carbon atoms. Optionally, B is a saturated alkylene chain, and the saturated alkylene is optionally non-substituted (e.g., $CH_2$, $CH_2CH_2$). Alternatively, the saturated alkylene chain may be substituted. In some embodiments, the saturated alkylene chain is substituted by hydroxy.

According to some embodiments, the ester moiety comprises a bulky group (i.e., comprising at least 3 carbon atoms and/or heteroatoms, optionally at least 4, and optionally at least 5 carbon atoms and/or heteroatoms) which is an alkyl, alkenyl or alkynyl group (represented by variable D), such that D is alkyl, alkenyl or alkynyl and B is absent. In some embodiments, the alkyl, alkenyl or alkynyl group is devoid of an aryl, heteroaryl, heteroalicyclic or cycloalkyl substituent.

As used herein throughout, the term "alkyl" refers to a saturated aliphatic hydrocarbon including straight chain and branched chain groups. Preferably, the alkyl group has 1 to 20 carbon atoms. Whenever a numerical range, e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, nitrile, nitro, azide, phosphonyl, phosphinyl, oxo, carbonyl, thiocarbonyl, urea, thiourea, carbamyl, N-carbamyl, O-thiocarbamyl, N-thiocarbamyl, C-amido, N-amido, C-carboxy, O-carboxy, sulfonamido, and amino, as these terms are defined herein.

An "alkenyl" group refers to an unsaturated aliphatic hydrocarbon which comprises at least one carbon-carbon double bond, including straight chain and branched chain groups. Preferably, the alkenyl group has 2 to 20 carbon atoms. More preferably, the alkenyl is a medium size alkenyl having 2 to 10 carbon atoms. Most preferably, unless otherwise indicated, the alkenyl is a lower alkenyl having 2 to 5 carbon atoms. The alkenyl group may be substituted or unsubstituted. When substituted, the substituent group can be, for example, cycloalkyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, nitrile, nitro, azide, phosphonyl, phosphinyl, oxo, carbonyl, thiocarbonyl, urea, thiourea, carbamyl, N-carbamyl, O-thiocarbamyl, N-thiocarbamyl, C-amido, N-amido, C-carboxy, O-carboxy, sulfonamido, and amino, as these terms are defined herein.

An "alkynyl" group refers to an unsaturated aliphatic hydrocarbon which comprises at least one carbon-carbon triple bond, including straight chain and branched chain groups. Preferably, the alkynyl group has 2 to 20 carbon atoms. More preferably, the alkynyl is a medium size alkynyl having 2 to 10 carbon atoms. Most preferably, unless otherwise indicated, the alkynyl is a lower alkynyl having 2 to 4 carbon atoms. The alkynyl group may be substituted or unsubstituted. When substituted, the substituent group can be, for example, cycloalkyl, alkenyl, aryl, heteroaryl, heteroalicyclic, halo, hydroxy, alkoxy, aryloxy, thiohydroxy, thioalkoxy, thioaryloxy, sulfinyl, sulfonyl, sulfonate, nitrile, nitro, azide, phosphonyl, phosphinyl, oxo, carbonyl, thiocarbonyl, urea, thiourea, carbamyl, N-carbamyl, O-thiocarbamyl, N-thiocarbamyl, C-amido, N-amido, C-carboxy, O-carboxy, sulfonamido, and amino, as these terms are defined herein.

In some embodiments, D is alkyl.

The alkyl is optionally non-substituted. n-Butyrate and isobutyrate are exemplary ester moieties wherein D is non-substituted alkyl.

Alternatively, the alkyl may be substituted. In some embodiments, the alkyl is substituted by oxo, hydroxy, alkoxy and/or C-carboxy. Exemplary ester moieties comprising substituted alkyl (without an aryl, heteroaryl, heteroalicyclic or cycloalkyl substituent) include pyruvate, azelate, and (2-methoxy-ethoxy)-acetate.

In some embodiments, D is alkenyl, for example, non-substituted alkenyl. 2-Hexenoate is an exemplary ester moiety wherein D is non-substituted alkenyl.

The substituents $R_a$-$R_d$ and $R_1$-$R_5$ are optionally selected such that hydrolysis of the esterified compound, i.e., conversion of one or more ester moieties to hydroxy, results in an active compound as described in International Patent Application PCT/IL2007/000404 (WO 2007/110868).

According to some embodiments, the bicyclic quinazolin-4-one moiety in Formula I is a non-substituted bicyclic moiety, such that each of $R_a$-$R_d$ is hydrogen.

Alternatively, at least one of $R_a$-$R_d$ is other than hydrogen, such that the bicyclic moiety is substituted.

In some embodiments, at least one of $R_a$-$R_d$ is selected from among alkyl, hydroxy, alkoxy and halide.

In some embodiments, $R_a$ is hydrogen or halide, short alkyl (being 1-4 carbon atoms in length) or short alkoxy (being 1-4 carbon atoms in length). In some embodiments, $R_a$ is hydrogen or halide. In some embodiments, the halide is chloride. In some embodiments, the alkyl is ethyl. In some embodiments, the alkoxy is methoxy.

In some embodiments, $R_b$ is hydrogen, halide (e.g., chloride), short alkyl (being 1-4 carbon atoms in length, and optionally being an aryl-substituted alkyl, e.g., benzyl), or alkoxy (being 1-4 carbon atoms in length, e.g., methoxy). In some embodiments, the alkyl is ethyl, propyl, trifluoromethyl or benzyl. In some embodiments, Rb is hydrogen, halide or alkoxy. According to exemplary embodiments, Rb is hydrogen or halide. In some embodiments, the halide is chloride. In some embodiments, the alkoxy is methoxy.

In some embodiments, Rc is hydrogen, alkoxy (being 1-4 carbon atoms in length), halide or alkyl (being 1-4 carbon atoms in length). In some embodiments, Rc is hydrogen, halide or alkyl. In some embodiments, the alkyl is methyl. In some embodiments, the halide is fluoride.

In some embodiments, Rd is hydrogen or alkyl. In some embodiments, the alkyl is methyl or propyl.

According to exemplary embodiments, Ra, Rc and Rd are each hydrogen.

According to some embodiments, one of $R_1$-$R_5$ is an ester moiety as defined herein and the others are hydrogen. In some embodiments, at least $R_1$ is such an ester moiety.

Alternatively, one or more of $R_1$-$R_5$ (optionally only one of $R_1$-$R_5$) is a substituent (i.e., a group other than hydrogen) other than the ester moiety described herein. Optionally, the one or more substituent(s) is alkyl, hydroxy, alkoxy, halide and/or nitrile.

Each of the compounds described herein can further be in a form of a pharmaceutically acceptable salt thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of the present embodiments, a pharmaceutically acceptable salt of the compounds described herein may optionally be an acid addition salt comprising at least one amine group of the compound (e.g., an amine group in a piperazine moiety) which is in a form of an ammonium ion (e.g., a quaternary ammonium ion), in combination with at least one counter ion, derived from the selected acid, that forms a pharmaceutically acceptable salt.

Depending on the stoichiometric proportions between the base (the amine group(s)) and the acid in the salt, the acid additions salts can be either mono-addition salts or poly-addition salts.

The phrase "mono-addition salt", as used herein, refers to a salt in which the stoichiometric ratio between the acid anion and amine cation is 1:1, such that the acid addition salt includes one molar equivalent of the acid per one molar equivalent of the compound.

The phrase "poly-addition salt", as used herein, refers to a salt in which the stoichiometric ratio between the acid anion and the amine cation is greater than 1:1 and is, for example, 2:1, 3:1, 4:1 and so on, such that the acid addition salt includes two or more molar equivalents of the acid per one molar equivalent of the compound.

The acid addition salts of the compounds described herein are therefore complexes formed between one or more amino groups of the drug and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined hereinabove.

Further, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The present embodiments further encompass any stereoisomers (enantiomers and diastereomers) of the compounds described herein, as well as any isomorph thereof.

As used herein, the terms "amine" and "amino" refer to a —NR'R" group, wherein R' and R" are selected from the group consisting of hydrogen, alkyl, cycloalkyl, heteroalicyclic (bonded through a ring carbon), aryl and heteroaryl (bonded through a ring carbon). Optionally, R' and R" are selected from the group consisting of hydrogen and alkyl comprising 1 to 4 carbon atoms. Optionally, R' and R" are hydrogen.

A "hydroxy" group refers to an —OH group.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "disulfide" group refers to both a —S-thioalkoxy and a —S-thioaryloxy group.

A "carbonyl" group refers to a —C(=O)—R' group, where R' is defined as hereinabove.

A "thiocarbonyl" group refers to a —C(=S)—R' group, where R' is as defined herein.

A "carboxy" group encompasses C-carboxy and O-carboxy groups, as defined herein.

A "C-carboxy" group refers to a —C(=O)—O—R' group, where R' is as defined herein.

An "O-carboxy" group refers to an R'C(=O)—O— group, where R' is as defined herein.

A "carboxylic acid" group refers to a C-carboxy group in which R' is hydrogen.

A "thiocarboxy" or "thiocarboxylate" group refers to both —C(=S)—O—R' and —O—C(=S)R' groups.

A "sulfonate" group refers to both —S(=O)$_2$—O—R' and —O—S(=O)$_2$—R' groups, where R' is as defined herein.

An "ester" refers herein to both carboxy esters and sulfonate esters.

A "carboxy ester" refers to an O-carboxy group attached to a carbon atom.

A "sulfonate ester" refers to a —O—S(=O)$_2$—R' sulfonate group attached to a carbon atom.

A "halide" or "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses O-thiocarbamyl and N-thiocarbamyl groups.

A thiocarbamate bond describes a —O—C(=S)—NR'— bond, where R' is as described herein.

A "C-amido" group refers to a —C(=O)—NR'R" group, where each of R' and R" is as defined herein.

An "N-amido" group refers to an R'C(=O)—NR"— group, where each of R' and R" is as defined herein.

An "amide" group encompasses both C-amido and N-amido groups.

A "nitro" group refers to an —NO$_2$ group.

A "nitroso" group refers to an —NO group.

A "nitrile" or "cyano" group refers to a —C≡N group.

An "isonitrile" group refers to a —N≡C group.

An "oxo" group refers to a =O group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

The term "phosphinyl" describes a —PR'R" group, with each of R' and R" as defined hereinabove.

A "urea" group refers to an —N(R')—C(=O)—NR"R'" group, where each of R' and R" is defined herein, and R'" is defined as R' and R" are defined herein.

The term "thiourea" describes a —N(R')—C(=S)—NR"— group, with each of R' and R" as defined hereinabove.

As used herein, the term "epoxide" describes a

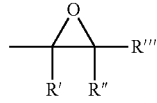

group, where R', R" and R'" are as defined herein.

As used herein, the term "thiirane" describes a group that is equivalent to an epoxide, wherein the oxygen atom of the epoxide is replaced with a sulfur atom.

As used herein, the term "aziridine" describes a group that is equivalent to an epoxide, wherein the oxygen atom of the epoxide is replaced with a nitrogen atom, and the nitrogen atom binds, in addition to two adjacent carbon atoms, R"", wherein R"" is defined according to the same definition as R'.

The term "hydrazine", as used herein, describes a —NR'-NR"R'" group, with R', R" and R'" as defined herein.

According to some embodiments of the present invention, each of the compounds described in the above-described embodiments of the present invention is for use in the treatment of a sexual disorder in a subject in need thereof.

Hence, according to another aspect of some embodiments the present invention, there is provided a method of treating a sexual disorder. The method, according to these embodiments of the present invention is effected by administering to a subject in need thereof a therapeutically effective amount of a compound having Formula I or a pharmaceutically acceptable salt thereof, as described herein.

As used herein the terms "treating", "treatment" and any grammatical diversion thereof include abrogating, substantially inhibiting, slowing or reversing the progression of a condition, substantially ameliorating clinical or aesthetical symptoms of a condition or substantially preventing the appearance of clinical or aesthetical symptoms of a condition.

Administering the compound can be effected via a transdermal, transmucosal oral, buccal, inhalation, parenteral and/or rectal route.

In some embodiments, the compound is administered transdermally.

As used herein the terms "transdermal" and "transdermally" refer to administration of a compound across the skin of a subject for systemic distribution.

Herein, a "therapeutically effective amount" means an amount of one or more of the compounds of the present invention sufficiently effective to prevent, alleviate or ameliorate symptoms of disease or prolong the survival of the subject being treated.

The amount of the compound to be administered can depend on the regimen (e.g., the time period between administration and the expected sexual activity) and on the pharmacokinetics of the compound, for example, a half-life of the administered compound and/or a product of hydrolysis of the administered compound in plasma, and/or a rate of absorption of an administered compound (e.g., when administered transdermally). Optionally, a desired plasma level of the administered compound at the expected time of sexual activity is determined (e.g., based on clinical studies in human subjects), and the time of administration and administered dose are determined accordingly. For example, if the time between administration and the expected sexual activity is approximately equal to the half-life of the compound in plasma, the therapeutically effective amount administered to the subject may be twice the desired plasma level during sexual activity. Preferably, the time between administration and expected sexual activity is selected so as to allow for a desired plasma level during sexual activity without necessitating administration of excessive (e.g., potentially toxic) doses of a compound.

As used herein the phrase "sexual disorder", also referred to herein and in the art as "sexual dysfunction", describes a medical condition that is expressed by a difficulty during any stage of the sexual act (which includes desire, arousal, orgasm, and resolution) that prevents an individual or couple from enjoying sexual activity. The medical condition can be associated with a mental malfunction, a physical malfunction and/or can be as a result of a medication, a drug, alcohol, and other external factors.

Sexual disorders are generally classified into the following categories: sexual desire disorders (decreased libido), sexual arousal disorders (e.g., erectile dysfunction, female sexual arousal disorder), and orgasm disorders (e.g., expressed by delay or absence of orgasm following a normal sexual excitement phase).

The subject is preferably a mammal, more preferably a human.

According to optional embodiments, the subject is a female subject. When the subject is female, the sexual disorder treated by the method is optionally selected from the group consisting of decreased libido, female sexual arousal disorder, and orgasm disorder.

The hydroxy-containing compounds described herein and the esterified derivatives thereof described herein were found particularly effective at treating sexual disorders in female subjects. As discusses hereinabove, treatment of sexual disorders according to current methodologies (e.g., PDE5 inhibitors) has been generally less successful in female subjects than in male subjects. In contrast, it was surprisingly uncovered that compounds according to embodiments of the invention are effective in females, and moreover, can be more effective in female than in males.

Hence, according to another aspect of embodiments of the invention, there is provided a method of treating a sexual disorder (e.g., as described herein) in a female subject, the method comprising administering (e.g., by transdermal administration) to the female subject a therapeutically effective amount of a compound of the general formula:

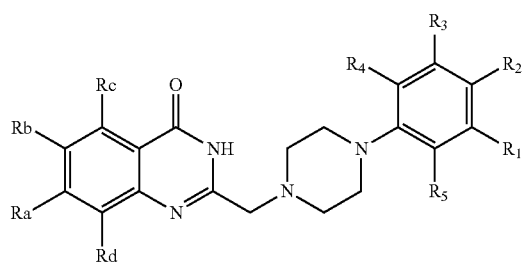

wherein at least one of $R_1$-$R_5$ is selected from the group consisting of hydroxy and an ester moiety having the above general Formula II, and Ra-Rd and $R_1$-$R_5$ are otherwise as defined hereinabove with respect to general Formula I.

In some embodiments, at least $R_1$ is hydroxy or an ester moiety.

According to another aspect of embodiments of the invention, there is provided a use of a compound described herein in the manufacture of a medicament for treating a sexual disorder (e.g., as described herein) in a subject. In some embodiments, the subject is a female subject. Optionally, the medicament is formulated for transdermal administration.

The methods and uses described herein can optionally be effected by combining a use of the compounds described herein with a use of other agents for treating sexual disorders (e.g., additional active agents that act as PDE-5 inhibitors or D4 agonists), or, alternatively, by use of the compounds described herein in combination with a drug which is known to cause a sexual dysfunction (e.g., serotonin reuptake inhibitors), in order to reduce or prevent the adverse effect of the drug in this regard.

In any of the methods and uses described herein, the compounds presented herein, can be utilized either per se, or, preferably as a part of a pharmaceutical composition.

Hence, according to another aspect of the present invention, there are provided pharmaceutical compositions, which comprise one or more of the compounds described above and a pharmaceutically acceptable carrier.

As used herein a "pharmaceutical composition" refers to a preparation of one or more of the compounds described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions described herein according to various embodiments of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the abovementioned compounds into preparations which, can be used pharmaceutically. Proper formulation is dependent upon the route of administration chosen.

According to optional embodiments, the pharmaceutical composition is formulated for transdermal administration.

As exemplified in the Examples section below, pharmaceutical compositions formulated for transdermal administration, such as are described herein, are effective at enhancing uptake of a compound for treating a sexual disorder (e.g., as described herein) into the bloodstream, and can therefore provide a long lasting, therapeutically effective concentration of the compound in plasma. Such a transdermal formulation may be formulated with any of a variety of compounds, including, but not limited to, esterified compounds such as those having Formula I (as described herein). Thus, for example, the advantageous effect of the transdermal formulation may be used in addition to, or instead of, the advantageous effect of the ester moiety described herein.

Hence, according to another aspect of embodiments of the invention, there is provided a pharmaceutical composition formulated for transdermal administration, the composition comprising a compound having the general Formula III:

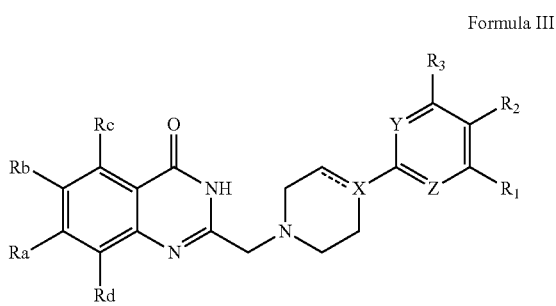

Formula III or a pharmaceutically acceptable salt thereof,
wherein:
the dashed line denotes a saturated or non-saturated bond;
X is selected from the group consisting of CH, C and N such that when X is C the dashed line denotes a non-saturated bond and when X is CH or N the dashed line denotes a saturated bond;
Y is N or $CR_4$ (e.g., $CR_4$);
Z is N or $CR_5$ (e.g., $CR_5$); and
Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, and a pharmaceutically acceptable carrier.

In exemplary embodiments, X is N, and the dashed line denotes a saturated bond.

Optionally, the compound having Formula III comprises at least one ester moiety (e.g., in accordance with Formula I, as described herein), for example, wherein at least one of $R_1$-$R_5$ is selected from the group consisting of carboxy (i.e., a carboxy ester) and sulfonate (i.e., a sulfonate ester). Optionally, the ester moiety has the general Formula II, as described herein. In some embodiments, $R_1$ is an ester moiety.

A composition comprising such a compound may optionally combine the advantageous effects of an ester moiety and of transdermal formulation, as described herein.

Alternatively or additionally, the compound having Formula III comprises at least one hydroxy group, for example, wherein at least one of $R_1$-$R_5$ is hydroxy. Optionally, the compound is obtainable by hydrolysis (i.e., conversion of one or more ester moieties to hydroxy) of a compound having general Formula I, as described herein. In some embodiments, $R_1$ is hydroxy.

A composition comprising such a compound may exhibit an advantageous enhancement of uptake of an active agent, which is associated with transdermal formulation, without need for gradual release of an active agent by hydrolysis of an esterified compound.

According to exemplary embodiments, the compound comprises a phenyl ring, wherein Y is $CR_4$ and Z is $CR_5$.

Optionally, Ra-Rd in Formula III are each independently as described herein with respect to Formula I.

Similarly, $R_1$-$R_5$ in Formula III are optionally each independently as described herein with respect to Formula I, with the exception that a compound according to Formula III need not include an ester moiety among $R_1$-$R_5$, as described herein.

By selecting the appropriate carrier and optionally other ingredients that can be included in the composition, as is detailed herein, the pharmaceutical compositions described herein may be formulated into any form suitable for topical application such as for transdermal administration. Hence, the pharmaceutical compositions can be, for example, in a form of a cream, an ointment, a paste, a gel, a lotion, and a soap. Ointments are semisolid preparations, typically based on vegetable oil (e.g. shea butter and/or cocoa butter), petrolatum or petroleum derivatives. As with other carriers or vehicles, an ointment base should be inert, stable, nonirritating and nonsensitizing.

Lotions are preparations that may to be applied to the skin without friction. Lotions are typically liquid or semiliquid preparations with a water or alcohol base, for example, an emulsion of the oil-in-water type. Lotions are typically preferred for treating large areas, due to the ease of applying a more fluid composition.

Creams are viscous liquids or semisolid emulsions, either oil-in-water or water-in-oil. Cream bases typically contain an oil phase, an emulsifier and an aqueous phase. The oil phase, also called the "lipophilic" phase, optionally comprises petrolatum and/or a fatty alcohol such as cetyl or stearyl alcohol. The aqueous phase optionally contains a humectant. The emulsifier in a cream formulation is optionally a nonionic, anionic, cationic or amphoteric surfactant.

Pastes are semisolid dosage forms which, depending on the nature of the base, may be a fatty paste or a paste made from a single-phase aqueous gel. The base in a fatty paste is generally petrolatum, hydrophilic petrolatum and the like. The pastes made from single-phase aqueous gels generally incorporate carboxymethylcellulose or the like as a base.

Gel formulations are semisolid, suspension-type systems. Single-phase gels contain organic macromolecules distributed substantially uniformly throughout the carrier liquid, which is typically aqueous, but also, preferably, contains a non-aqueous solvent and, optionally, an oil. Preferred organic macromolecules, i.e., gelling agents, are crosslinked acrylic acid polymers such as the family of carbomer polymers, e.g., carboxypolyalkylenes that may be obtained commercially under the trademark CARBOPOL™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

A pharmaceutical composition formulated for transdermal administration may optionally be present in a patch, a swab, a pledget, and/or a pad.

Transdermal patches and the like may comprise some or all of the following components: a pharmaceutical composition (e.g., as described herein), a liner for protecting the patch during storage, which is optionally removed prior to use, an adhesive for adhering different components together and/or adhering the patch to the skin, a backing which protects the patch from the outer environment, and/or a membrane which controls release of a drug into the skin.

According to optional embodiments, the pharmaceutical composition is in a form of an oil-in-water emulsion. The oil-in-water emulsion may be, for example, in the form of a lotion or a cream.

As used herein and in the art, an "oil-in-water emulsion" is an emulsion characterized by a lipophilic phase which is dispersed within an aqueous phase.

According to some embodiments, the lipophilic phase of the emulsion comprises at least one solvent selected from the group consisting of propylene glycol, propylene glycol monolaurate (e.g., Lauroglycol 90) and propylene glycol laurate (e.g., Lauroglycol FCC).

In some embodiments, the lipophilic phase further comprises at least one solubilizing agent, for example, at least one solubilizing agent selected from the group consisting of lauroyl macrogolglycerides (e.g., lauroyl macrogol-32 glycerides), which are also known in the art as lauroyl polyoxyl glycerides. Exemplary lauroyl macrogolglycerides are available as Gelucire® 44/14.

In some embodiments, the composition further comprises at least one surfactant, for example, at least one surfactant selected from the group consisting of phosphatidyl choline and caprylocapryl macrogolglycerides (e.g., caprylocaproyl polyoxyl-8 glycerides). Exemplary caprylocapryl macrogolglycerides are available as Labrosol®.

In some embodiments, the composition further comprises macrogolglycerol stearate (e.g., stearoyl macrogol-32 glycerides), which are also known in the art as stearoyl macrogolglycerides or stearoyl polyoxyl glycerides. Exemplary macrogolglycerol stearate is available as Gelucire® 50/13.

The solvent and/or additional components of the emulsion (e.g., such as described herein) are optionally selected so as to allow for at least a desired solubility (optionally, at least 10 mg per 1 gram) of a compound described herein in the composition.

The solvent and additional components are preferably selected so as to be non-toxic when applied transdermally.

In some embodiments, the emulsion comprises from 60 to 97.5 weight percents of a lipophilic phase, and optionally from 70 to 90 weight percents.

Herein, ingredients of the composition which are soluble in a lipophilic phase are considered components of the lipophilic phase (regardless of whether the ingredient undergoes partitioning between a lipophilic phase and the aqueous phase). Similarly, a weight percent of a lipophilic phase refers herein to a sum of the weights of the components of the lipophilic phase, as defined herein.

According to optional embodiments, the lipophilic phase of the composition comprises propylene glycol, propylene glycol monolaurate (e.g., Lauroglycol 90), lauroyl macrogolglycerides (e.g., Gelucire® 44/14), phosphatidyl choline, caprylocapryl macrogolglycerides (e.g., Labrasol®) and macrogolglycerol stearate (Gelucire® 50/13).

In an exemplary embodiment, the composition as a whole comprises from 25 to 75 weight percents propylene glycol, from 8 to 30 weight percents lauroyl macrogolglycerides (e.g., Gelucire® 44/14), from 1 to 4 weight percents caprylocapryl macrogolglycerides (e.g., Labrasol®), from 1 to 4 weight percents propylene glycol monolaurate (e.g., Lauroglycol 90) from 2.5 to 10 weight percents macrogolglycerol stearate (e.g., Gelucire® 50/13), and from 3 to 12 weight percents phosphatidyl choline.

According to optional embodiments, the composition further comprises vitamin E TPGS (α-tocopheryl polyethylene glycol succinate), for example, at a concentration of up to 1 weight percent of the composition.

In some embodiments, the composition further comprises a sustained-release agent (e.g., a water-soluble sustained-release agent in the aqueous phase of the emulsion). Suitable sustained-release agents are commercially available. Optionally, the sustained-release agent is a thickening agent (optionally a gelling agent described herein). Carboxymethyl cellulose is an exemplary sustained-release agent.

As exemplified herein, pharmaceutical compositions formulated for transdermal administration as described herein may comprise a relatively high concentration of a compound described herein (e.g., a compound having Formula III), for example, a concentration of at least 10 mg of the compound per 1 gram of the pharmaceutically effective carrier therein.

According to optional embodiments, the pharmaceutical composition is stable (e.g., devoid of substantial chemical changes and/or phase separation) at room temperature (e.g., 20° C.) for at least 2 weeks, optionally at least 1 month, optionally at least 2 months, optionally at least 6 months, and optionally at least 1 year.

As described herein, transdermal pharmaceutical compositions described herein provide for a continuous release of the compound into the blood stream of a subject. In some embodiments, the pharmaceutical composition is characterized by an ability to release the compound (e.g., a compound according to Formula III) for at least 2 hours, optionally for at least 3 hours, optionally for at least 4 hours, and optionally for at least 6 hours, upon administration of the composition on a skin of a subject.

Release of a compound from an applied composition may be determined quantitatively by any suitable technique used in the art.

Optionally, the release is determined in vivo, by monitoring plasma concentrations of the compound. Using standard pharmacokinetic analysis, the absorption of a compound into the plasma may be determined for each point in time, based on the observed concentration of the compound in plasma and on the rate of clearance of the compound.

Alternatively, the release may be determined in vitro, by monitoring permeation of a compound through skin in a Franz diffusion cell.

Herein, a composition is considered to be able to release a compound for a particular period of time (e.g., at least two hours) if the rate at which the compound permeates the skin (e.g., absorption into plasma) during the period of time is at least half of the maximal rate achieved after administration of the composition.

According to another aspect of embodiments of the invention, there is provided a method of treating a sexual disorder (e.g., a sexual disorder described herein) comprising transdermally administering to a subject (e.g., as described herein) in need thereof a therapeutically effective amount of a pharmaceutical composition formulated for transdermal administration, as described herein.

Alternatively, compounds of embodiments of the invention may be formulated for routes of administration other than transdermal administration.

For injection, the compounds of embodiments of the invention may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the compounds of embodiments of the invention can be formulated readily by combining the compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the compounds for use according to the present invention are conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compounds of the present invention and a suitable powder base such as, but not limited to, lactose or starch.

The compounds described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the compounds of the present invention prepared in water-soluble form. Additionally, suspensions of the compounds may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds to allow for the preparation of highly concentrated solutions.

Alternatively, the compounds of the present invention may be in powder form for constitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of embodiments of the present invention include compositions wherein the active ingredients are contained in a therapeutically effective amount for achieving the intended purpose. Determination of a therapeutically effective amount is well within the capability of those skilled in the art, especially in light of the detailed disclosure provided herein.

For any compound used in the methods of the invention, the therapeutically effective amount or dose can be estimated initially from activity assays in animals. For example, a dose can be formulated in animal models (e.g., in an animal model of transdermal administration) to achieve a circulating concentration range that has been shown by activity assays to result in significant D4 receptor binding and/or activation, and/or significant enhancement of sexual arousal and/or activity (e.g., as determined by monitoring vaginal or penile blood flow). Such information can be used to more accurately determine useful doses in humans.

Toxicity and therapeutic efficacy of the compounds described herein can be determined by standard pharmaceutical procedures in experimental animals, e.g., by determining the $EC_{50}$, the $IC_{50}$ and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the desired effects, termed the minimal effective concentration (MEC). The MEC will vary for each preparation, but can be estimated from in vitro data; e.g., the concentration necessary to achieve 50-90% of the maximal level of D4 receptor activation. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of a sexual disorder (e.g., as described herein).

Thus, according to some embodiments of the present invention, the pharmaceutical compositions described herein are packaged in a packaging material and identified in print, in or on the packaging material, for use in the treatment of a sexual disorder (e.g., a disorder as described herein) in a subject in need thereof. In some embodiments, the pharmaceutical composition is identified for use in the treatment of a sexual order in a female subject, as described herein.

As used herein the term "about" refers to ±10%.

The terms "comprises", "comprising", "includes", "including", "having" and their conjugates mean "including but not limited to".

The term "consisting of means "including and limited to".

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:
2-Amino-5-chlorobenzamide was obtained from Sigma-Aldrich;
Anthranilamide was obtained from Sigma-Aldrich;
Benzoyl chloride (99%) was obtained from Sigma-Aldrich;
Carboxymethyl cellulose was obtained from Aqualon (France);
2-chloro-1,1,1-trimethoxyethane was obtained from Sigma-Aldrich;
N,N'-Dicyclohexylcarbodiimide (99%) was obtained from Fluka;
Dimethylformamide (>99%) was obtained from BioLab (Israel);
Ethylacetate (>99%) was obtained from BioLab;
Gelucire® 44/14 (lauroyl polyoxyl-32 glycerides) was obtained from Gattefosse (France);
Gelucire® 50/13 (macrogolglycerol stearates) was obtained from Gattefosse;
Hexane (>99%) was obtained from BioLab;
1-(3-hydroxyphenyl)piperazine was obtained from Alfa-Aesar;
1-(4-hydroxyphenyl)piperazine was obtained from Alfa-Aesar;
Labrosol® (caprylocaproyl polyoxyl-8 glycerides) was obtained from Gattefosse;
Lauroglycol 90 (propylene glycol monolaurate) was obtained from Gattefosse;
Lauroglycol FCC (propylene glycol laurate) was obtained from Gattefosse;
4-Methoxyphenylacteic acid (99%) was obtained from Sigma-Aldrich;

Phosphatidyl choline was obtained from Lipoid (Germany);

Propylene glycol was obtained from MP Biomedical (France);

Toluene (>99%) was obtained from BioLab;

Triethylamine (99%) was obtained from Sigma-Aldrich;

Vitamin E TPGS (α-tocopheryl polyethylene glycol succinate) was obtained from Eastman (UK).

Synthesis of R-55 (2-((4-(3-hydroxyphenyl)piperazin-1-yl)methyl)quinazolin-4-one)

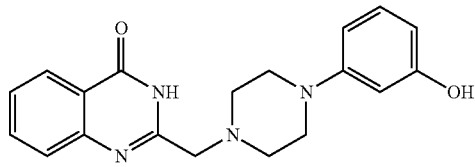

R-55

11.1 grams (81.6 mmol) of anthranilamide and 18 grams (122.4 mmol) of 2-chloro-1,1,1-trimethoxyethane were dissolved in 100 ml of toluene and stirred at a temperature of 80° C. A catalytic amount of p-toluene sulfonic acid was added, and the temperature was maintained at 80° C. for an additional 30 minutes. A precipitate formed, which was filtered and dried to yield 15.5 grams of an intermediate. 21.7 grams (118 mmol) of 1-(3-hydroxyphenyl)piperazine, 150 ml of dimethylformamide, and 12.5 ml of triethylamine were then added, and the mixture was stirred at room temperature for 24 hours. The solvent was evaporated under reduced pressure, and the residue was purified on silica gel (100% ethyl acetate), yielding 15 grams of R-55.

Synthesis of L-215 (6-chloro-2-((4-(3-hydroxyphenyl)piperazin-1-yl)methyl)quinazolin-4-one)

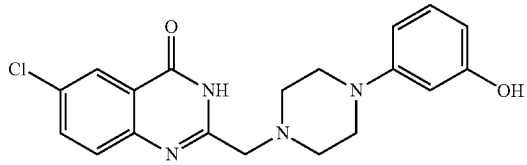

L-215

L-215, a chlorinated derivative of R-55, was synthesized in a manner analogous to the synthesis of R-55.

5 grams (29.3 mmol) of 2-amino-5-chlorobenzamide and 6.8 grams (44 mmol) of 2-chloro-1,1,1-trimethoxyethane were dissolved in 50 ml of toluene and stirred at a temperature of 80° C. A catalytic amount of p-toluene sulfonic acid was added, and the temperature was maintained at 80° C. for an additional 30 minutes. A precipitate formed, which was filtered and dried to yield 6.58 grams of an intermediate. 6.17 grams (34.6 mmol) of 1-(3-hydroxyphenyl)piperazine, 100 ml of dimethylformamide, and 7 ml of triethylamine were then added, and the mixture was stirred at room temperature for 24 hours. The solvent was evaporated under reduced pressure, and the residue was purified on silica gel (100% ethyl acetate), yielding 4.92 grams of L-215.

Synthesis of L-221 (2-((4-(4-hydroxyphenyl)piperazin-1-yl)methyl)quinazolin-4-one)

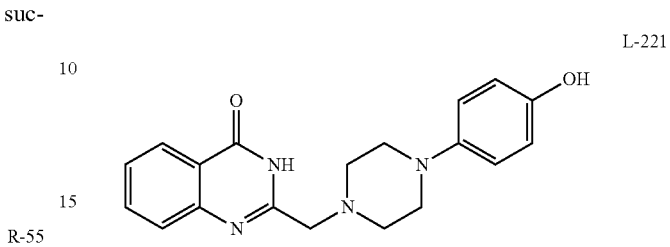

L-221

L-221, a regioisomer of R-55 which comprises a 4-hydroxyphenyl moiety instead of a 3-hydroxyphenyl moiety, was synthesized in a manner analogous to the synthesis of R-55.

3.52 grams (26 mmol) of anthranilamide and 5.1 grams (37.2 mmol) of 2-chloro-1,1,1-trimethoxyethane were dissolved in 50 ml of toluene and stirred at a temperature of 80° C. A catalytic amount of p-toluene sulfonic acid was added, and the temperature was maintained at 80° C. for an additional 30 minutes. A precipitate formed, which was filtered and dried to yield 5.9 grams of an intermediate. 4.6 grams (25.8 mmol) of 1-(4-hydroxyphenyl)piperazine, 50 ml of dimethylformamide, and 5 ml of triethylamine were then added, and the mixture was stirred at room temperature for 24 hours. The solvent was evaporated under reduced pressure, and the residue was purified on silica gel (100% ethyl acetate), yielding 3.78 grams of L-221.

Synthesis of L-238 (2-((4-(2-hydroxyphenyl)piperazin-1-yl)methyl)quinazolin-4-one)

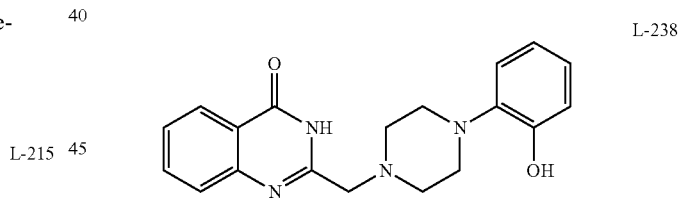

L-238

6.44 grams (47 mmol) of anthranilamide and 10.9 grams (67.5 mmol) of 2-chloro-1,1,1-trimethoxyethane were dissolved in 50 ml of toluene and stirred at a temperature of 80° C. A catalytic amount of p-toluene sulfonic acid was added, and the temperature was maintained at 80° C. for an additional 30 minutes. A precipitate formed, which was filtered and dried to yield 9.3 grams of an intermediate. 10 grams (56.1 mmol) of 1-(2-hydroxyphenyl)piperazine, 100 ml of dimethylformamide, and 10 ml of triethylamine were then added, and the mixture was stirred at room temperature for 24 hours. The solvent was evaporated under reduced pressure, and the residue was purified on silica gel (100% ethyl acetate), yielding 4.15 grams of L-238.

Liquid Chromatography-Mass Spectrometry (LCMS) Analysis:

R-55 and related compounds were assayed in the plasma samples using a Waters (USA) Alliance high performance liquid chromatograph coupled with a Waters Micromass ZQ quadruple mass spectrometer (in ESI+ mode) as a detector with Waters Empower chromatographic and mass spectrometric software for chromatographic data acquisition, processing and instrument control.

The tested compound was extracted from plasma using dichloromethane, followed by concentration by evaporating the extract and dissolution in a low volume chromatographic mobile phase.

The instrument was calibrated using plasma spiked with various concentrations of the tested compound. Enrofloxacin (m/z=360.4) was used as an internal standard.

Example 1

Pharmacokinetics of R-55 Following Intravenous Administration

In order to investigate the pharmacokinetics of R-55, the presence of R-55 in plasma was measured following intravenous administration of R-55 in pigs.

White Landrace female pigs were acclimatized for 2 days prior to treatment. 3 pigs were administered 0.2 mg/kg R-55 by intravenous injection at a dose volume of 0.2 ml/kg. Blood samples were withdrawn from each pig via a jugular vein catheter at the following time points: immediately prior to injection (t=0), and 5 minutes, 10 minutes, 15 minutes, 30 minutes, 45 minutes, 60 minutes, 90 minutes, 2 hours, 3 hours, 4 hours, and 6 hours post-injection. All samples were collected in a K3EDTA tube (Greiner). Blood samples were stored on crushed ice after collection. Plasma was separated by centrifugation (10 minutes at 3000 rotations per minute), within two hours post-sampling. Each plasma sample was divided into two aliquots before freezing. Plasma samples were then stored at −20° C. until being dispatched for LCMS analysis.

Clinical observations were performed during the six hours following application. No abnormal side effects were observed in any pig during this period.

Pharmacokinetic analysis was performed using the WIN-NONLIN version 5.0 (Pharsight, USA) computerized software. Area under curves of concentration vs. time (AUC) were calculated using the log linear trapezoidal rule. Area under curves were determined for the time period for which concentrations were measured, i.e., t=0 to 6 hours ($AUC_{all}$), and for an infinite time period ($AUC_{INF}$), as determined by extrapolation of the curve to t=∞.

The R-55 plasma levels are summarized in Table 1. No R-55 was detected in the plasma of any of the pigs 45 minutes or more following administration.

TABLE 1

R-55 plasma levels following intravenous administration in pigs

| Time after injection | R-55 plasma concentration (ng/ml) | | |
|---|---|---|---|
| | Animal #1 | Animal #2 | Animal #3 |
| 0 minutes | 0 | 0 | 0 |
| 5 minutes | 157.8 | 122.1 | 142.2 |
| 10 minutes | 86.7 | 112.9 | 83.0 |
| 15 minutes | 30.4 | 76.8 | 52.8 |
| 30 minutes | 0 | 24.9 | 22.3 |

The pharmacokinetic parameters are summarized in Table 2 below.

TABLE 2

Pharmacokinetics of R-55 following intravenous administration in pigs

| Parameter | Animal #1 | Animal #2 | Animal #3 |
|---|---|---|---|
| $T_{1/2}$ - half-life (minutes) | 8.67 | 10.34 | 9.67 |
| $C_{max}$ - maximal concentration (ng/ml) | 157.8 | 122.1 | 142.2 |
| $AUC_{all}$ (minutes*ng/ml) | 1676.5 | 2129.0 | 1821.3 |
| $AUC_{INF}$ (minutes * ng/ml) | 1926.6 | 2501.3 | 2132.2 |
| Clearance (ml/minutes/kg) | 103.8 | 80.0 | 93.8 |
| Volume of distribution (ml/kg) | 1298.1 | 1193.0 | 1308.1 |
| Volume of distribution at steady state (ml/kg) | 1507.1 | 1358.9 | 1509.3 |
| Mean residence time (minutes) | 14.5 | 17.0 | 15.8 |

As shown in Tables 1 and 2, R-55 was eliminated from the bloodstream within approximately 30 minutes after administration, with the half-life of R-55 being about 9-10 minutes. The AUC of R-55 was about 1900-1500 minutes·ng/ml.

These results indicate that the efficacy of R-55 could be increased by providing a longer lifetime of R-55 in plasma.

Example 2

Esterified Derivatives of R-55

In a search for heterocyclic compounds that would exhibit improved pharmacokinetic profile, and improved bioavailability in particular (longer period of effective plasma concentration), ester derivatives of R-55 were synthesized, with the aim of obtaining slow release of the heterocyclic compound upon hydrolysis of the esters.

R-55 was synthesized as described hereinabove. Ester derivatives of R-55 were prepared via two synthetic pathways.

In one synthetic pathway, R-55 and an equimolar amount of a carboxylic acid are esterified by Stieglich esterification, using DCC (N,N'-dicyclohexylcarbodiimide) as a coupling agent, as shown in Scheme 1 below.

Scheme 1

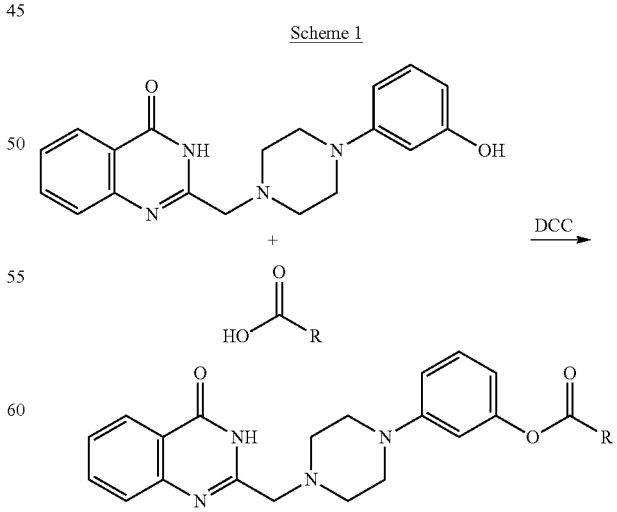

In a typical example, 672 mg (2 mmol) of R-55 in 0.5 ml dimethylformamide (DMF) was added to a solution of 332 mg (2 mmol) 4-methoxyphenylacetic acid and 122 mg (1 mmol) 4-dimethylaminopyridine in 7 ml of dichloromethane. The resulting mixture was stirred in an ice bath. To this solution, 412 mg (2 mmol) DCC dissolved in 2 ml of dichloromethane was added portion-wise over the course of an hour while stirring the ice bath. The resulting mixture was subsequently stirred at room temperature for another 3 hours. Ethyl acetate was then added, the precipitate was filtered, and the filtrate was evaporated under reduced pressure. The obtained residue was purified on silica gel (50% hexane/50% ethyl acetate). 400 mg of the product, named L-170, was obtained. The yield was 41%. The purity of the product was determined by LCMS (liquid chromatography-mass spectrometry) to be 96.3%.

L-170

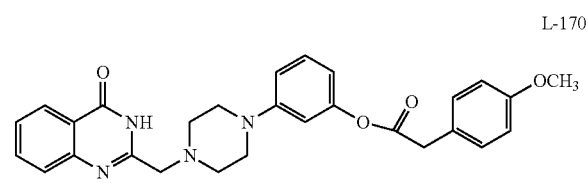 [SMILES: COc1ccc(CC(=O)Oc2cccc(N3CCN(Cc4nc5ccccc5c(=O)[nH]4)CC3)c2)cc1]

Using essentially the same procedures, R-55 was esterified with the following acids (product names are in parentheses):

5-methyl-2-pyrazine carboxylic acid (L-172);

5-hydroxyanthranilic acid (L-175);

tetrahydro-2-furoic acid (L-177);

pyrrole-2-carboxylic acid (L-179);

3-methylsalicylic acid (L-181);

4-chloromandelic acid (L-183);

2-hydroxy-3-isopropyl benzoic acid (L-189);

pyruvic acid (L-191);

3,4-diaminobenzoic acid (L-196);

trans-2-hexenoic acid (L-200);

1-naphthoic acid (L-201);

azelaic acid (L-202);

p-toluylacetic acid (L-203);

salicylic acid (L-204);

4-methylsalicylic acid (L-205);

5-methylsalicylic acid (L-206);

2-nitrobenzoic acid (L-208);

3-nitrobenzoic acid (L-210);

4-oxo-1H-1-benzopyran-2-carboxylic acid (L-211);

cholic acid (L-212);

3-aminopyrazine-2-carboxylic acid (L-214);

4-amino-2,3,5,6-tetrafluorobenzoic acid (L-219);

3-aminobenzoic acid (L-222);

fluorene-1-carboxylic acid (L-224);

2,3,4,5,6-pentafluorophenyl acetic acid (L-241).

In an alternative synthetic pathway, an acyl chloride was reacted with an equimolar amount of R-55, as shown in Scheme 2 below.

Scheme 2

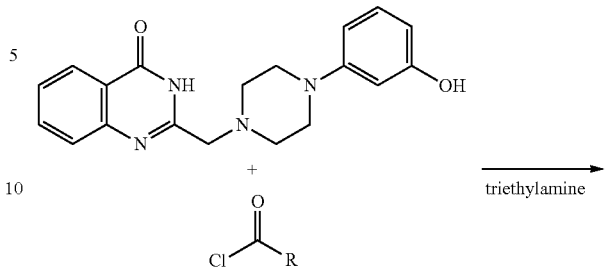

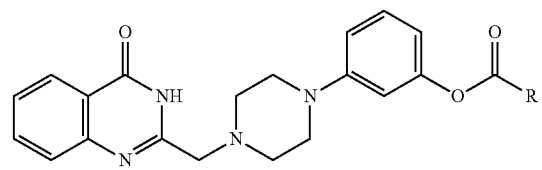

In a typical example, 672 mg (2 mmol) of R-55 and 232 µl (2 mmol) of benzoyl chloride were dissolved in 15 ml of chloroform with 240 µl triethylamine A catalytic amount of 4-dimethylaminopyridine (DMAP) was added and the mixture was stirred at 60° C. for 24 hours. The solvent was then evaporated under reduced pressure and the obtained residue was purified on silica gel (50% hexane/50% ethyl acetate). 670 mg of the product, named L-207, was obtained. The yield was 74%. The purity of the product was determined by LCMS to be over 99%.

$^1$H NMR (500 MHz, CDCl$_3$): 9.97 (s, 1H), 8.32 (d, 1H, ArH), 8.22 (t, 1H, ArH), 7.79-7.53 (m, 7H, ArH), 6.86 (d, 1H, ArH), 6.77 (m, 2H, ArH), 3.67 (s, 2H, CH2), 3.33 (t, 4H, CH2 piperazine), 2.79 (t, 4H, CH2 piperazine).

$^{13}$C NMR: 165.21, 161.58, 153.02, 152.09, 151.97, 148.88, 134.79, 133.55, 130.17, 129.91, 128.57, 127.15, 126.89, 126.65, 113.48, 113.00, 109.51, 60.60, 53.27, 48.85.

The compound was soluble in dimethylformamide, dimethyl sulfoxide, tetrahydrofuran, chloroform, dichloromethane, and HCl in diethyl ether, and non-soluble in water.

L-207

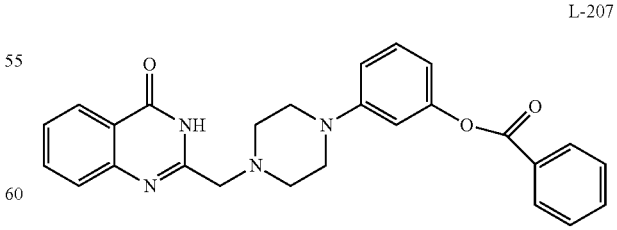

Using essentially the same procedure, R-55 was esterified with various commercially available acyl chlorides. The acyl chlorides and products obtained therefrom are summarized in Table 3.

TABLE 3
Acyl and sulfonyl chlorides and esterified derivatives of R-55 obtained therefrom
| Acyl chloride | Product |
|---|---|
| 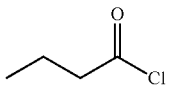<br>n-butyl chloride | 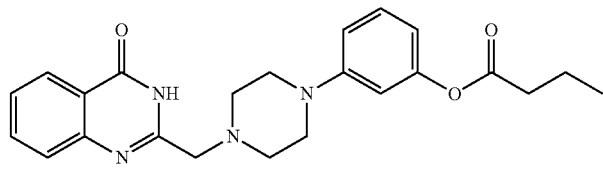 [SMILES: CCCC(=O)Oc1cccc(N2CCN(Cc3nc4ccccc4c(=O)[nH]3)CC2)c1]<br>L-124<br>(18% yield) |
| 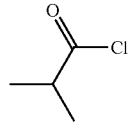<br>isobutyl chloride | 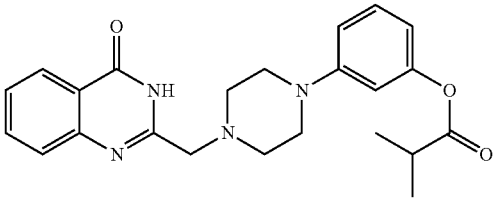 [SMILES: CC(C)C(=O)Oc1cccc(N2CCN(Cc3nc4ccccc4c(=O)[nH]3)CC2)c1]<br>L-127<br>(16% yield) |
| 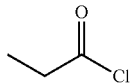<br>propionyl chloride | 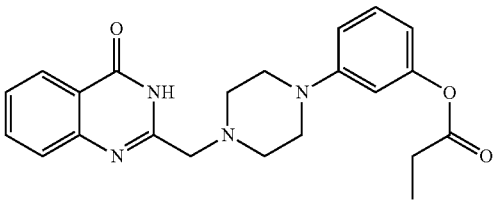 [SMILES: CCC(=O)Oc1cccc(N2CCN(Cc3nc4ccccc4c(=O)[nH]3)CC2)c1]<br>L-128<br>(14% yield) |
| 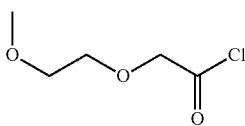<br>(2-methoxy-ethoxy)-<br>acetyl chloride | 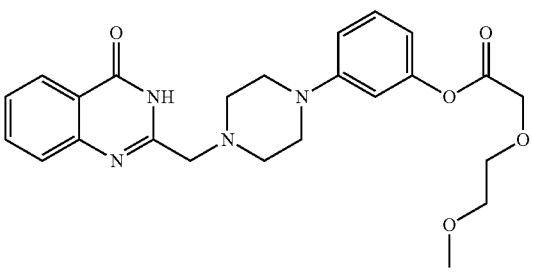 [SMILES: COCCOCC(=O)Oc1cccc(N2CCN(Cc3nc4ccccc4c(=O)[nH]3)CC2)c1]<br>L-141<br>(16% yield) |
| 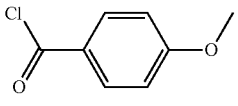<br>4-methoxybenzoyl<br>chloride | 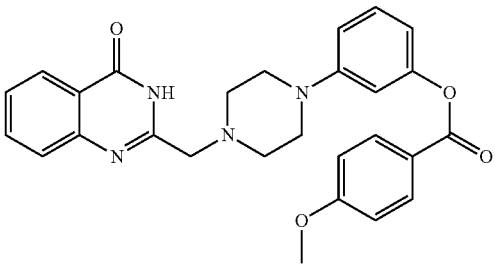 [SMILES: COc1ccc(C(=O)Oc2cccc(N3CCN(Cc4nc5ccccc5c(=O)[nH]4)CC3)c2)cc1]<br>L-162<br>(68% yield) |

TABLE 3-continued
Acyl and sulfonyl chlorides and esterified derivatives of R-55 obtained therefrom
| Acyl chloride | Product |
|---|---|
| 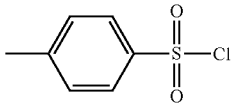<br>p-toluenesulfonyl chloride | 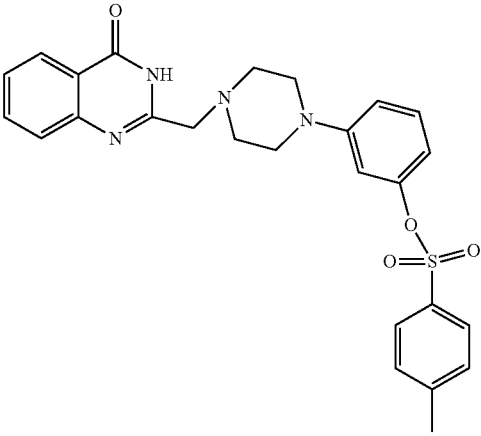 [SMILES: Cc1ccc(S(=O)(=O)Oc2cccc(N3CCN(Cc4nc5ccccc5c(=O)[nH]4)CC3)c2)cc1]<br>L-163<br>(75% yield) |
| <br>methanesulfonyl chloride | 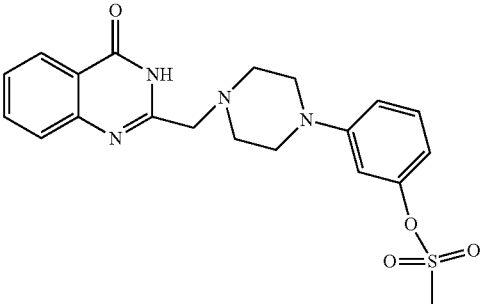 [SMILES: CS(=O)(=O)Oc1cccc(N2CCN(Cc3nc4ccccc4c(=O)[nH]3)CC2)c1]<br>L-164<br>(55% yield) |
| 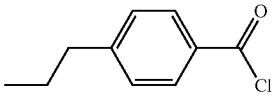<br>4-propylbenzoyl chloride | 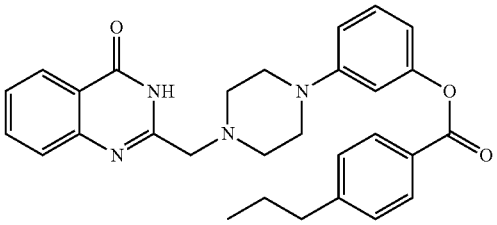 [SMILES: CCCc1ccc(C(=O)Oc2cccc(N3CCN(Cc4nc5ccccc5c(=O)[nH]4)CC3)c2)cc1]<br>L-165<br>(58% yield) |
| 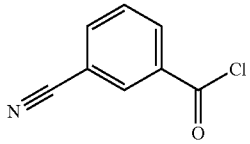 [SMILES: N#Cc1cccc(C(=O)Cl)c1]<br>3-cyanobenzoyl chloride | 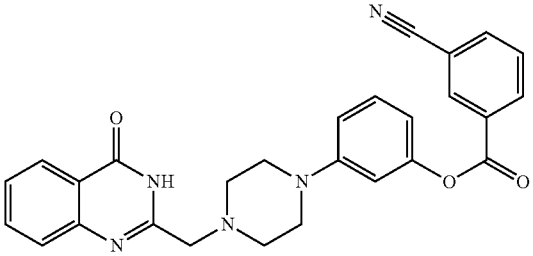 [SMILES: N#Cc1cccc(C(=O)Oc2cccc(N3CCN(Cc4nc5ccccc5c(=O)[nH]4)CC3)c2)c1]<br>L-166<br>(70% yield) |

TABLE 3-continued
Acyl and sulfonyl chlorides and esterified derivatives of R-55 obtained therefrom
| Acyl chloride | Product |
|---|---|
| 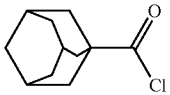 [SMILES: O=C(Cl)C12CC3CC(CC(C3)C1)C2]<br>1-adamantanecarbonyl chloride | 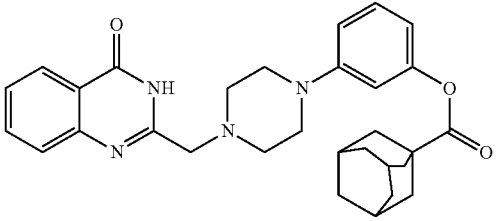 [SMILES: O=C(Oc1cccc(N2CCN(Cc3nc4ccccc4c(=O)[nH]3)CC2)c1)C12CC3CC(CC(C3)C1)C2]<br>L-167<br>(60% yield) |
| 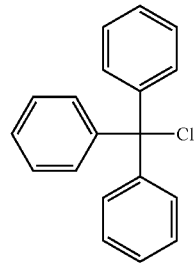 [SMILES: ClC(c1ccccc1)(c1ccccc1)c1ccccc1]<br>triphenylchloromethane | 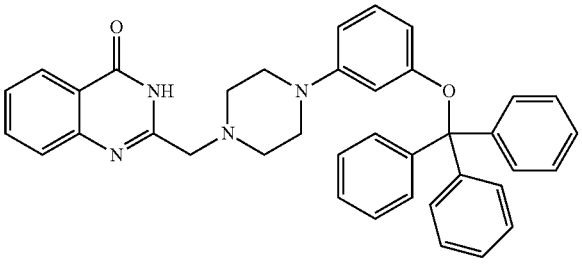 [SMILES: O=c1[nH]c(CN2CCN(c3cccc(OC(c4ccccc4)(c4ccccc4)c4ccccc4)c3)CC2)nc2ccccc12]<br>L-168<br>(52% yield) |
| 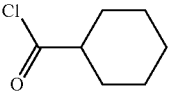<br>cyclohexanecarbonyl chloride | 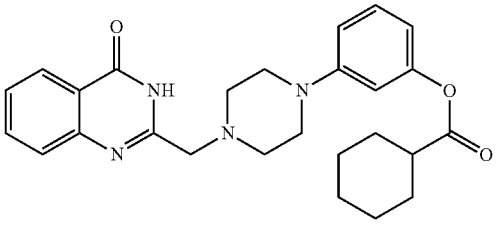 [SMILES: O=C(Oc1cccc(N2CCN(Cc3nc4ccccc4c(=O)[nH]3)CC2)c1)C1CCCCC1]<br>L-169<br>(75% yield) |
| 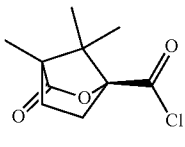<br>(1S)-(−)-camphanic chloride | 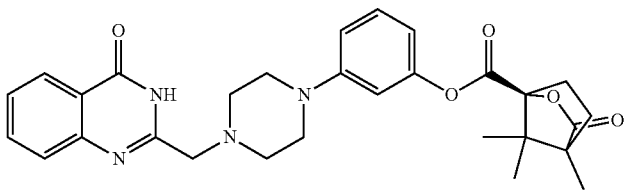 [SMILES: CC12CC[C@](C(=O)Oc3cccc(N4CCN(Cc5nc6ccccc6c(=O)[nH]5)CC4)c3)(OC1=O)C2(C)C]<br>L-171<br>(82% yield) |
| 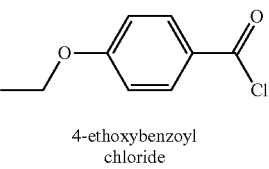<br>4-ethoxybenzoyl chloride | 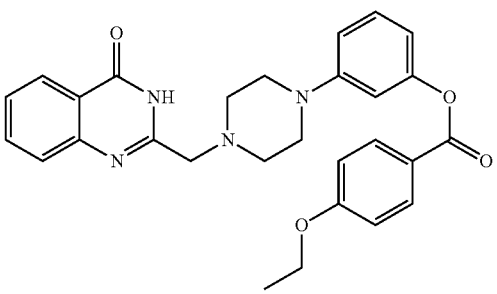 [SMILES: CCOc1ccc(C(=O)Oc2cccc(N3CCN(Cc4nc5ccccc5c(=O)[nH]4)CC3)c2)cc1]<br>L-173<br>(77% yield) |

TABLE 3-continued
Acyl and sulfonyl chlorides and esterified derivatives of R-55 obtained therefrom
| Acyl chloride | Product |
| --- | --- |
| 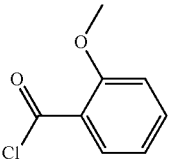<br>2-methoxybenzoyl chloride | 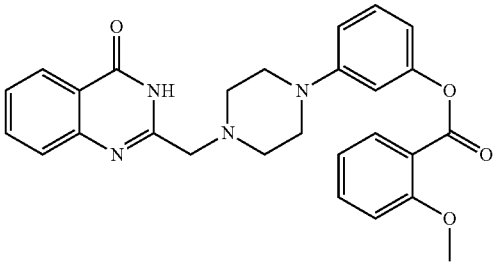 [SMILES: COc1ccccc1C(=O)Oc1cccc(N2CCN(Cc3nc4ccccc4c(=O)[nH]3)CC2)c1]<br>L-174<br>(39% yield) |
| 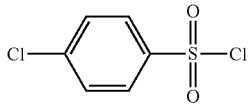<br>4-chlorobenzenesulfonyl chloride | 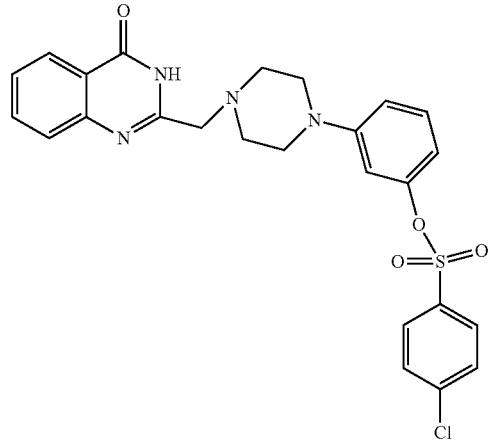 [SMILES: O=c1[nH]c(CN2CCN(c3cccc(OS(=O)(=O)c4ccc(Cl)cc4)c3)CC2)nc2ccccc12]<br>L-176<br>(67% yield) |
| 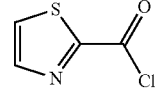<br>1,3-thiazole-2-carbonyl chloride | 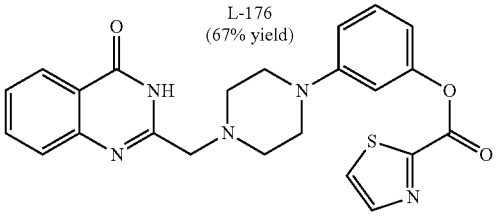 [SMILES: O=C(Oc1cccc(N2CCN(Cc3nc4ccccc4c(=O)[nH]3)CC2)c1)c1nccs1]<br>L-178<br>(56% yield) |
| 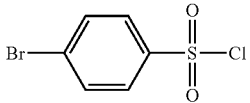 [SMILES: O=S(=O)(Cl)c1ccc(Br)cc1]<br>4-bromobenzenesulfonyl chloride | 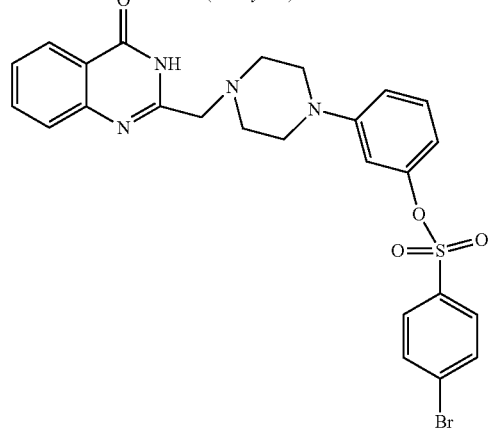<br>L-180<br>(78% yield) |

TABLE 3-continued

Acyl and sulfonyl chlorides and esterified derivatives of R-55 obtained therefrom

| Acyl chloride | Product |
|---|---|
| 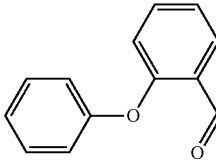<br>2-phenoxybenzoyl chloride | 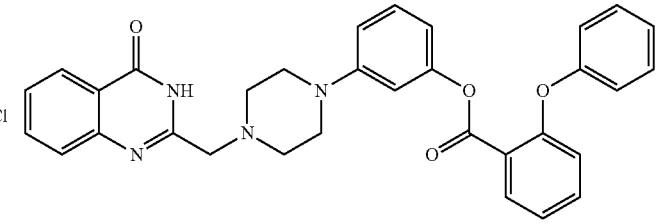<br>L-188<br>(10% yield) |
| 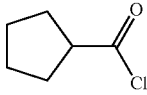<br>cyclopentanecarbonyl chloride | 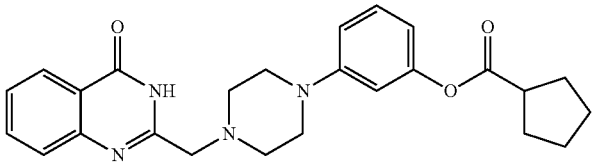 [SMILES: O=C(Oc1cccc(N2CCN(Cc3nc4ccccc4c(=O)[nH]3)CC2)c1)C1CCCC1]<br>L-190<br>(36% yield) |
| 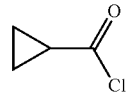<br>cyclopropanecarbonyl chloride | 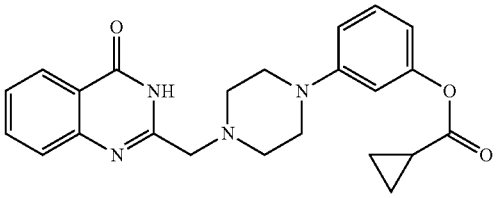 [SMILES: O=C(Oc1cccc(N2CCN(Cc3nc4ccccc4c(=O)[nH]3)CC2)c1)C1CC1]<br>L-194<br>(62% yield) |
| 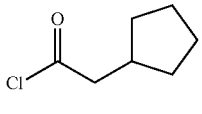<br>cyclopentylacetyl chloride | 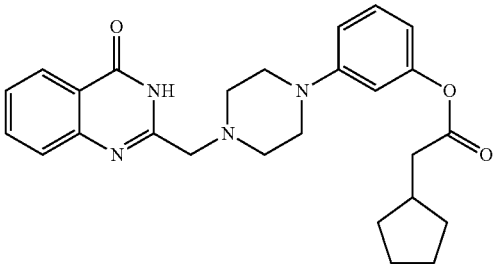 [SMILES: O=C(CC1CCCC1)Oc1cccc(N2CCN(Cc3nc4ccccc4c(=O)[nH]3)CC2)c1]<br>L-197<br>(72% yield) |
| 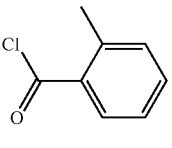<br>o-toluoyl chloride | 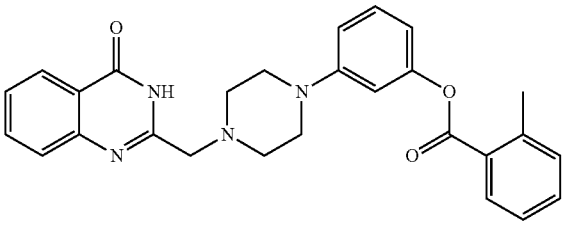 [SMILES: Cc1ccccc1C(=O)Oc1cccc(N2CCN(Cc3nc4ccccc4c(=O)[nH]3)CC2)c1]<br>L-199<br>(65% yield) |

TABLE 3-continued

Acyl and sulfonyl chlorides and esterified derivatives of R-55 obtained therefrom

| Acyl chloride | Product |
|---|---|
| benzoyl chloride | L-207 (78% yield) |
| 4-fluorobenzoyl chloride | L-209 (65% yield) |

Example 3

Esterified Derivatives of Additional Active Agents

L-215, L-221 and L-238 were synthesized as described hereinabove, and esterified derivatives of these compounds were synthesized in order to obtain slow release of the compounds upon hydrolysis of the esters.

Esterified Derivatives of L-215:

In one method, L-215 and an equimolar amount of a carboxylic acid are esterified by Stieglich esterification, using DCC (N,N'-dicyclohexylcarbodiimide) as a coupling agent, as described in Example 2 for R-55.

Using essentially the same procedures as described in Example 2, L-215 was esterified with the following acids (product names are in parentheses):
 4-methoxyphenyl acetic acid (L-218);
 p-tolylacetic acid (L-235);
 salicylic acid (L-244).

In an alternative method, an acyl chloride was reacted with an equimolar amount of L-215, as described in Example 2 for R-55.

Using essentially the same procedures as described in Example 2, L-215 was esterified using the following acyl chlorides (product names are in parentheses):
 cyclohexanecarbonyl chloride (L-216);
 cyclopentanecarbonyl chloride (L-217);
 cyclopropanecarbonyl chloride (L-220);
 cyclopentylacetyl chloride (L-223);
 1-adamantanecarbonyl chloride (L-234);
 (1S)-(−)-camphanic chloride (L-236);
 benzoyl chloride (L-239);
 2-methoxybenzoyl chloride (L-245);
 4-fluorobenzoyl chloride (L-250).

Esterified Derivatives of L-221:

In one method, L-221 and an equimolar amount of a carboxylic acid are esterified by Stieglich esterification, using DCC (N,N'-dicyclohexylcarbodiimide) as a coupling agent, as described above for R-55.

Using essentially the same procedures as described in Example 2, L-221 was esterified with the following acids (product names are in parentheses):
 4-methoxyphenyl acetic acid (L-231);
 p-tolylacetic acid (L-251).

In an alternative method, an acyl chloride was reacted with an equimolar amount of L-221, as described in Example 2 for R-55.

Using essentially the same procedures as described in Example 2, L-215 was esterified using the following acyl chlorides (product names are in parentheses):
 cyclohexanecarbonyl chloride (L-225);
 cyclopentanecarbonyl chloride (L-226);
 cyclopropanecarbonyl chloride (L-227);
 cyclopentylacetyl chloride (L-228);
 1-adamantanecarbonyl chloride (L-233);
 (1S)-(−)-camphanic chloride (L-237);
 benzoyl chloride (L-240);
 2-methoxybenzoyl chloride (L-252);
 4-fluorobenzoyl chloride (L-253).

Esterified Derivatives of L-238:

In one method, L-238 and an equimolar amount of a carboxylic acid are esterified by Stieglich esterification, using DCC (N,N'-dicyclohexylcarbodiimide) as a coupling agent, as described above for R-55.

Using essentially the same procedures as described in Example 2, L-238 was esterified with the following acids (product names are in parentheses):
 4-methoxyphenyl acetic acid (L-242);
 p-tolylacetic acid (L-246).

In an alternative method, an acyl chloride was reacted with an equimolar amount of L-238, as described in Example 2 for R-55.

Using essentially the same procedures as described in Example 2, L-238 was esterified using the following acyl chlorides (product names are in parentheses):

cyclohexanecarbonyl chloride (L-249);
cyclopentanecarbonyl chloride (L-254);
1-adamantanecarbonyl chloride (L-255);
benzoyl chloride (L-243);
2-methoxybenzoyl chloride (L-247);
4-fluorobenzoyl chloride (L-248).

Example 4

Half-Lives of Esterified Derivatives of R-55 in Plasma

The half-lives of various esterified derivative of R-55 in human and rat plasma were determined, in order to ascertain the rate at which the esterified derivative releases R-55 via hydrolysis.

50 µl of dimethyl sulfoxide containing 0.2 mg of the tested derivative was added to 1 ml of fresh plasma (human or rat) in a sterile Eppendorf tube. The samples were then incubated at 37° C., and 100 µl samples were removed at various times, up to 120 minutes after incubation. The plasma samples were immediately added to 1 ml acetonitrile. After vigorous mixing by vortex, the samples were centrifuged for 10 minutes at 2000 rotations per minute at 4° C. 0.95 ml of the supernatant was then removed and stored at −20° C. until determination of the concentrations of R-55 and its esterified derivative by LCMS analysis.

Exemplary results for one derivative (L-207) are presented in Example 2. Based on the data presented in Table 4, the half-life of L-207 in human plasma was calculated to be 134 minutes, whereas the half-life of L-207 in rat plasma was calculated to be 29 minutes.

TABLE 4

Hydrolysis of L-207 to R-55 in human and rat plasma

| Time | Human plasma | | Rat plasma | |
| --- | --- | --- | --- | --- |
| (minutes) | % R-55 | % L-207 | % R-55 | % L-207 |
| 0 | N.D. | N.D. | 0.51 | 99.49 |
| 10 | 2.46 | 97.54 | N.D. | N.D. |
| 15 | N.D. | N.D. | 25.92 | 74.08 |
| 30 | 10.79 | 89.21 | 52.27 | 47.73 |
| 60 | 22.89 | 77.11 | 93.39 | 6.61 |
| 90 | 35.33 | 64.67 | 99.24 | 0.76 |
| 120 | 47.09 | 52.91 | 99.51 | 0.41 |

N.D. = not determined

The measured half-lives for various derivatives of R-55 are summarized in Table 5 below.

TABLE 5

Half-lives ($T_{1/2}$) for hydrolysis of esterified derivatives of R-55 in human and rat plasma

| R-55 derivative | $T_{1/2}$ in human plasma (minutes) | $T_{1/2}$ in rat plasma (minutes) |
| --- | --- | --- |
| L-128 | 10 | 0.31 |
| L-162 | 377 | 54 |
| L-163 | >1000 | >1000 |
| L-164 | >1000 | >1000 |
| L-166 | 480 | 7.1 |
| L-167 | 750 | 58 |
| L-169 | 41 | 4.7 |
| L-170 | 280 | 7.5 |
| L-173 | >1000 | 16.5 |
| L-174 | 455 | 52 |
| L-179 | 150 | 3.3 |

TABLE 5-continued

Half-lives ($T_{1/2}$) for hydrolysis of esterified derivatives of R-55 in human and rat plasma

| R-55 derivative | $T_{1/2}$ in human plasma (minutes) | $T_{1/2}$ in rat plasma (minutes) |
| --- | --- | --- |
| L-199 | >1000 | 44 |
| L-204 | 380 | 25 |
| L-207 | 134 | 29 |
| L-209 | 470 | 35 |

As shown in Table 5, a broad range of half-lives can be obtained in plasma, depending on the acyl moiety in the ester.

In general, small non-substituted acyl moieties, such as propionyl (L-128), benzoyl (L-207), cyclohexanecarbonyl (L-169), and pyrrole-2-carbonyl (L-179) resulted in relatively rapid hydrolysis, with the smallest tested acyl moiety (propionyl) providing the most rapid hydrolysis. Bulky moieties such as 1-adamantanecarbonyl (L-167) resulted in relatively slow hydrolysis. Sulfonate esters (L-163, L-164) resulted in considerably slower hydrolysis than carboxyl esters.

The rate of hydrolysis was considerably affected by the substituents present on the aryl rings. For example, a 4-ethoxy substituent (L-173) resulted in a considerably slower hydrolysis than did the smaller, yet chemically similar 4-methoxy substituent (L-162). Furthermore, even relatively small substituents such as fluoro (L-209), hydroxy (L-204) and methoxy (L-162, L-174) consistently resulted in slower hydrolysis than exhibited by the corresponding non-substituted aryl (L-207).

In contrast, a linker attached to an aryl ring did not slow hydrolysis. Thus, 4-methoxyphenylacetyl (L-170) resulted in slower hydrolysis than did 4-methoxybenzoyl (L-162), although 4-methoxyphenylacetyl is a larger group than 4-methoxybenzoyl.

In addition, acyl moieties such as aryl (e.g., phenyl of L-207) and heteroaryl (e.g., pyrrol-2-yl of L-179) groups resulted in slower hydrolysis than did a cycloalkyl group of comparable size (e.g., cyclohexyl of L-169).

These results suggest that esterified derivatives of R-55 can gradually release R-55 into the human bloodstream over a course of several hours, and that the rate of release can be controlled by selection of an appropriate ester.

Example 5

Transdermal Formulation of R-55

Transdermal drug-delivery systems are placed on skin in order to deliver a specific dose of medication into the bloodstream. Transdermal delivery advantageously provides controlled release of a drug. However, transdermal release may be difficult to achieve, as the skin is a very effective barrier.

In order to effect transdermal delivery of R-55, a stable formulation comprising 1 to 10 mg/gram of R-55 in a gel-like suspension suitable for transdermal delivery was designed. The formulation was designed to be stable for at least one week. A gel-like suspension was designed in order to facilitate administration of the R-55 in the form of a patch.

To this effect, a stable oil-in-water emulsion was developed. Various solvents were tested in order to achieve an R-55 concentration of up to 20 mg/gram in the lipid phase of the emulsion, in order to achieve a total concentration of up to 10 mg/gram R-55.

The following organic solvents which are used in transdermal formulations were tested:
polyethylene glycols (PEG-200, PEG-400, PEG-2000);
propylene glycol;
triglycerides;
polyoxylglycerides.

Of the aforementioned solvents, propylene glycol (PG) was found to be the most effective solvent of R-55, although solubility was less than 5 mg/gram. Addition of phosphatidyl choline (PC) in a weight ratio of 4:1 PG:PC increased the solubility of R-55 to 8 mg/gram.

In order to obtain improved solubility, the following co-solvents were then tested:
oleoyl macrogolglycerides;
linoleoyl macrogolglycerides;
medium-chain triglycerides;
propylene glycol dicaprylocaprate (Labrafac PG);
propylene glycol monolaurate (Lauroglycol 90);
propylene glycol laurate (Lauroglycol FCC);
lauroyl macrogolglycerides (Gelucire® 44/14).

Of the aforementioned co-solvents, Lauroglycol 90, Lauroglycol FCC and Gelucire® 44/14 were found to be the most effective solubilizers of R-55.

Based on these results, propylene glycol, Lauroglycol 90, Lauroglycol FCC and Gelucire® 44/14 were selected for further study.

In order to obtain a lipid phase comprising at least about 12 mg/gram R-55, which is capable of self-emulsification as a suspension in an aqueous phase, various co-surfactants were tested for use in combination with phosphatidyl choline (PC). The following co-surfactants were tested:
caprylocaproyl macrogolglycerides (Labrasol®);
propylene glycol monocaprylate;
propylene glycol monolaurate;
polyglyceryl oleate.

A combination of PC and Labrasol® in a 3:1 ratio (w/w) was found to be particularly effective for self-emulsification.

In addition to the above-described ingredients, a sustained release agent was added to the formulation. Stearoyl macrogolglycerides (Gelucire® 50/13) were found to be a suitable sustained release agent.

Transdermal formulations were prepared from propylene glycol (solvent and penetration enhancer), Lauroglycol 90 (solubilizer, co-surfactant, penetration enhancer), Gelucire® 44/14 (solubilizer), phosphatidyl choline (surfactant), Labrasol® (co-surfactant, penetration enhancer), and Gelucire® 50/13 (sustained release agent).

The aqueous phase comprised 0.5% carboxymethyl cellulose, and represented 5% to 20% of the formulation.

Vitamin E TPGS (tocopheryl polyethyleneglycol succinate) was added as an optional stabilizer.

In an exemplary formulation comprising 10 mg/ml R-55, 50 grams propylene glycol, 16 grams Gelucire® 44/14, 2 grams Labrasol®, 2 grams Lauroglycol 90, 5 grams Gelucire® 50/13, 6 grams phosphatidyl choline, and 0.2 grams vitamin E TPGS were mixed by stirring at 40° C. until the phosphatidyl choline was completely dissolved (for approximately 2 hours), to form a lipid base. 1 gram of R-55 was then added to the lipid base, followed by stirring at 40° C. until complete dissolution of the R-55 (for approximately 3 hours). Approximately 18 grams of 0.5% aqueous solution of carboxymethyl cellulose was then added to obtain 100 grams of a suspension, which was stirred continuously at room temperature for approximately 10 hours.

The formulation was stable for at least 2 weeks at room temperature.

Example 6

Transdermal Administration of R-55

In order to investigate the feasibility of transdermal administration of R-55, the presence of R-55 in plasma was measured following administration to pigs of the exemplary transdermal formulation described in Example 5.

White Landrace female pigs were acclimatized for 5 days prior to application of the formulation. 50 ml of the formulation (containing 500 mg R-55) was applied over a 15×7 cm area of the skin of each pig, in a single dose. In order to facilitate constant transdermal administration for at least 6 hours, a suitable plastic shield, attached by adhesive plaster, was used to cover the whole treated dermal surface area for six hours.

Clinical observations were performed during the six hours following application. No clinical abnormalities were observed in any pig during this period.

Blood samples were withdrawn from each pig via a jugular vein catheter at the following time points: immediately prior to application (t=0) and 15 minutes, 30 minutes, 45 minutes, 60 minutes, 90 minutes, 2 hours, 4 hours, and 6 hours post-application. All samples were collected in commercially available, EDTA supplemented test-tubes. Blood samples were stored on crushed ice after collection. Plasma was separated by centrifugation (10 minutes at 3000 rotations per minute), within one hour post-sampling. Each plasma sample was divided into two aliquots before freezing. Plasma samples were then stored at −20° C. until being dispatched for LCMS analysis.

As shown in Table 6, in all 4 tested pigs, R-55 was found in plasma 30 minutes after application, and in 3 of the 4 tested pigs, R-55 was found in plasma two hours after application. In two pigs, R-55 was observed more or less continuously from 30 minutes to 2 hours after application.

TABLE 6

Plasma R-55 concentrations following transdermal administration of 500 mg R-55 in pigs

| Time after application | R-55 concentration (ng/ml) | | | |
| --- | --- | --- | --- | --- |
| | Animal #1 | Animal #2 | Animal #3 | Animal #4 |
| 0 minutes | 0 | 0 | 0 | 0 |
| 15 minutes | 0 | 0 | 10.8 | 0 |
| 30 minutes | 16.7 | 19.9 | 11.8 | 15.2 |
| 45 minutes | 0 | 0 | 0 | 10.5 |
| 60 minutes | 10.3 | 0 | 0 | 10.7 |
| 90 minutes | 16.8 | 0 | 0 | 10.1 |
| 2 hours | 14.8 | 11.8 | 0 | 10.7 |
| 4 hours | 0 | 0 | 0 | 0 |
| 6 hours | 0 | 0 | 0 | 0 |

These results suggest that transdermal administration of R-55 provides a relatively stable concentration of R-55 in plasma, for up to at least 2 hours after administration.

Example 7

Activity Assays for Dopamine Receptor Binding

R-55 (which comprises a 3-hydroxyphenyl moiety) and its isomers L-221 (comprising a 4-hydroxyphenyl moiety) and L-238 (comprising a 2-hydroxyphenyl moiety) were assayed for competitive binding to $D_{2\ SHORT}$ and $D_{4.4}$ type dopamine receptors, in order to assess their efficacy for treating sexual disorders. Both receptor types are expressed as human recombinant proteins in CHO cells, as described, for example, in Jarvis et al. (1973); Van Tol et al. (1991) and Van Tol et al. (1992).

Determination of binding to D2 short receptor was performed using [$^3$H]-spiperone, a D2 receptor ligand (Gundlach et al., 1984), as a radioligand (20-60 Ci/mmol, 0.2 nM) in the presence of various concentrations of the tested compound. Reactions were carried out in 50 mM TRIS-HCl (pH 7.4) containing 120 mM NaCl, 5 mM KCl, 5 mM MgCl$_2$ and 1 mM EDTA, for 60 minutes at 25° C. The reaction was terminated by rapid vacuum filtration onto glass fiber filters. Radioactivity trapped onto the filters was determined (counted) and compared to control values in order to accurately evaluate any interaction of the test compound(s) with the cloned dopamine D2 short binding site.

Determination of binding to D4.4 receptor was performed using [$^3$H]-YM-09151-2 (70-87 Ci/mmol, 0.3 nM), as a radioligand, in the presence of various concentrations of the tested compound. Reactions were carried out in 50 mM TRIS-HCl (pH 7.4) containing 5 mM MgCl$_2$, 5 mM EDTA, 5 mM KCl and 1.5 mM CaCl$_2$, for 60 minutes at 22° C. The reaction was terminated by rapid vacuum filtration onto glass fiber filters. Radioactivity trapped onto the filters was determined (counted) and compared to control values in order to accurately evaluate any interaction of the tested compound(s) with the cloned dopamine D4.4 binding site.

Selectivity of R-55 was calculated as the D4/D2 binding ratio, based on the ratio of the concentration required to inhibit 50% of the radioligand binding for each receptor.

TABLE 7

Competitive binding by exemplary compounds of D4.4 receptor and selectivity for D4 receptor

| Compound | IC$_{50}$ for binding of D4.4 (μM) | Selectivity D4/D2 |
|---|---|---|
| R-55 | 0.5 | 160 |
| L-238 | ~10 | N.D. |
| L-221 | ~30 | N.D. |

N.D. = not determined

As shown in Table 7, R-55 exhibits the strongest affinity to the D4 receptor, as well as the highest selectivity for the D4 receptor, although L-221 and L-238 also exhibit considerable affinity for the D4 receptor.

These results indicate that exemplary compounds such as R-55 can selectively bind to D4 dopamine receptors, and thereby enhance sexual function without causing excessive side effects.

Example 8

Activity Assays for Receptor and Enzyme Binding

R-55 (which comprises a 3-hydroxyphenyl moiety) and the structurally related compounds N-108 (2-{[4-(2-ethoxyphenyl)piperazin-1-yl]methyl}quinazolin-4(3H)-one) and B-39 (7-chloro-2-((5,6-dihydro-4-(2-methoxyphenyl)pyridin-1(2H)-yl)methyl)quinazolin-4(3H)-one) were assayed for competitive binding to a variety of receptors, including D$_{4.4}$ type dopamine receptor, in order to assess their specificity for D$_{4.4}$ dopamine receptors.

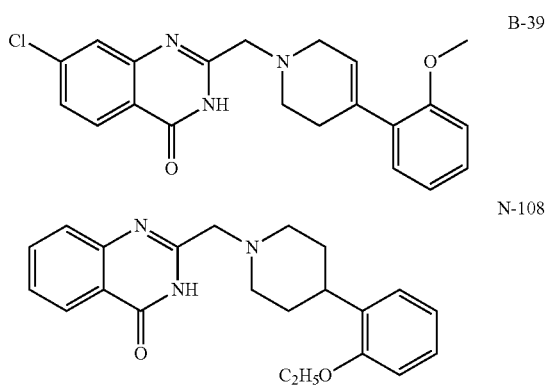

The receptors were expressed as human recombinant proteins in CHO cells, except for adrenergic $\alpha_1$ and $\alpha_2$ receptors which were expressed in Wistar rat brain and cerebral cortex cells, respectively, and melanocortin MC$_4$ receptor which was expressed in human recombinant HEK-293 cells. Binding was determined using the following radioligands in the presence of various concentrations of the tested compound:

0.25 nM prazosin for adrenergic $\alpha_1$ receptor,
0.7 nM rauwolscine for adrenergic $\alpha_2$ receptor,
0.05 nM)(Tyr$^0$)-corticotropin releasing factor (CRF) for corticotropin releasing factor CRF$_1$ receptor,
1.4 nM and 2 nM SCH-23390, respectively, for dopamine D$_1$ and D$_5$ receptors,
0.16 nM, 0.7 nM and 1.2 nM spiperone, respectively, for dopamine D$_{2S}$, D$_3$ and D$_{4.4}$ receptors,
0.02 nM NDP-α-MSH for melanocortin MC$_4$ receptor,
1.5 nM 8-OH-DPAT for serotonin 5-HT$_{1A}$ receptor, and
1 nM mesulergine for serotonin 5-HT$_{2C}$ receptor.

The binding assays were performed in accordance with procedures described in the literature (Greengrass & Bremner, 1979; Boyajian & Leslie, 1987; Broadhurst, 1988; Lewis, 2001; Sutton, 1995; Dearry, 1990; Zhou, 1990; Grandy, 1989; Hayes, 1992; Sokoloff, 1990; Van Tol, 1991; Van Tol 1992; Sunahara, 1991; Weinshank, 1991; Schioth, 1996; Schioth 1997; Martin & Humphrey, 1994; May, 2003; Wolf & Schutz, 1997).

As shown in Table 8, B-39, R-55 and N-108 each exhibited high binding affinity to the D$_{4.4}$ receptor, but R-55 exhibited low binding affinity to receptors other than D$_{4.4}$ receptor, in comparison to B-39 and N-108. Thus, B-39 and N-108 each exhibited high binding affinity to a variety of receptors other than D$_{4.4}$ receptor, including receptors for which binding is expected to cause deleterious side effects (e.g., serotonin receptors), whereas R-55 exhibited high binding affinity only to one receptor other than D$_{4.4}$ receptor.

TABLE 8

Competitive binding of B-39, R-55 and N-108 to various receptors

| Receptor | Competitive binding (%) at 5 μM of tested compound | | |
|---|---|---|---|
| | B-39 | R-55 | N-108 |
| Adrenergic $\alpha_1$ receptor | 54 | 10 | 73 |
| Adrenergic $\alpha_2$ receptor | 72 | 39 | 54 |
| CRF$_1$ receptor | −5 | 3 | −11 |
| Dopamine D$_1$ receptor | 4 | −12 | −6 |
| Dopamine D$_{2S}$ receptor | 46 | 7 | 28 |
| Dopamine D$_3$ receptor | 32 | 5 | 1 |

TABLE 8-continued

Competitive binding of B-39, R-55 and N-108 to various receptors

| Receptor | Competitive binding (%) at 5 μM of tested compound | | |
|---|---|---|---|
| | B-39 | R-55 | N-108 |
| Dopamine $D_{4.4}$ receptor | 57 | 31 | 57 |
| Dopamine $D_5$ receptor | 7 | 0 | 3 |
| Melanocortin $MC_4$ receptor | 5 | 3 | 4 |
| Serotonin $5\text{-}HT_{1A}$ receptor | 89 | 7 | 55 |
| Serotonin $5\text{-}HT_{2C}$ receptor | 56 | 5 | 21 |

In addition, R-55 and its hydrochloride salt were assayed for PARP (poly(ADP-ribose)polymerase) inhibitory activity, as some quinazolinone derivatives, particularly derivatives comprising quinazolinone linked via a three-carbon moiety to substituted pyridinyl and piperazinyl moieties, have been identified as potent PARP inhibitors [U.S. Patent Application Publication No. 2004/0077667; Iwashita et al., FEBS Lett 579:1389-1393(2005); Hattori et al., J Med Chem 47:4151-4154(2004)]. PARP plays a natural role in repair of DNA damage, and inhibition of PARP may lead to undesirable side effects in any treatment of a sexual disorder.

Inhibition of PARP-1 was assayed using a Universal Chemiluminescent PARP Assay (Trevigen, Inc.).

The tested compounds were diluted from 2.1 mg of powder in 25 μl of DMSO. The tested compounds were diluted to 100 μM in 1% DMSO/99% ethanol. 3-Aminobenzamide (3-AB), a commercially available weak PARP inhibitor, was used as a positive control. The activity of PARP was quantified as relative light units (RLU). Each of the tested compounds was assayed twice.

In Assay 1, the 100 μM stock solution was diluted to 40 μM in 1×PARP buffer. The compounds were then serially diluted down to 0.4 μM. Each tested compound was further diluted 1:4 during the assay, so the final concentrations ranged from 10 μM to 0.1 μM.

In Assay 2, the 100 μM stock was added to 1×PARP buffer to prepare samples with concentrations ranging from 40 μM to 2 μM. A 10 μM stock solution was added to 1×PARP buffer to prepare samples with concentrations of 1 μM and 0.4 μM. Each tested compound was further diluted 1:4 during the assay, so the final concentrations ranged from 10 μM to 0.1 μM.

Figure 1B:
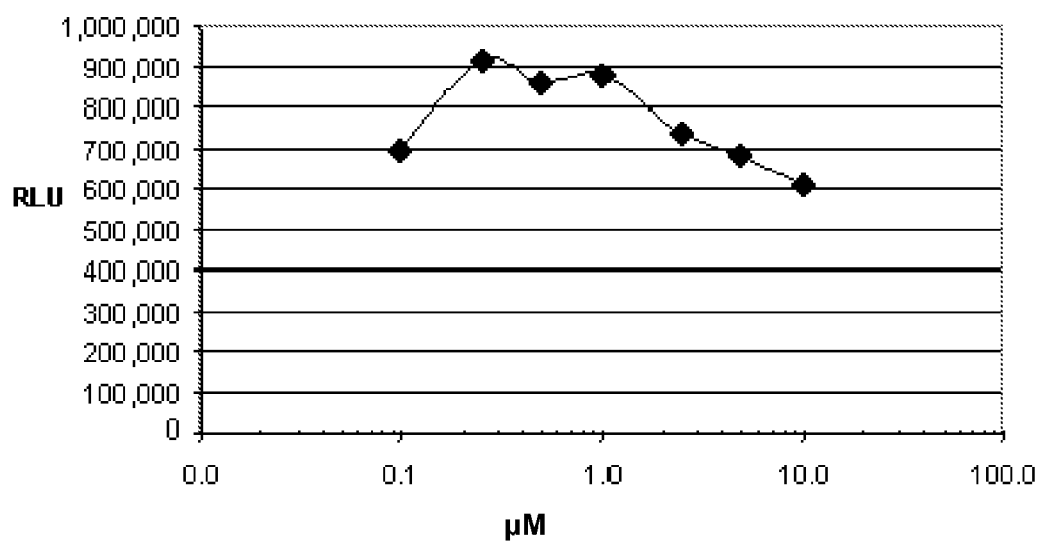

As shown in FIGS. 1A and 1B, R-55 did not exhibit any significant inhibition of PARP in either Assay 1 (FIG. 1A) or Assay 2 (FIG. 1B).

Figure 2A:
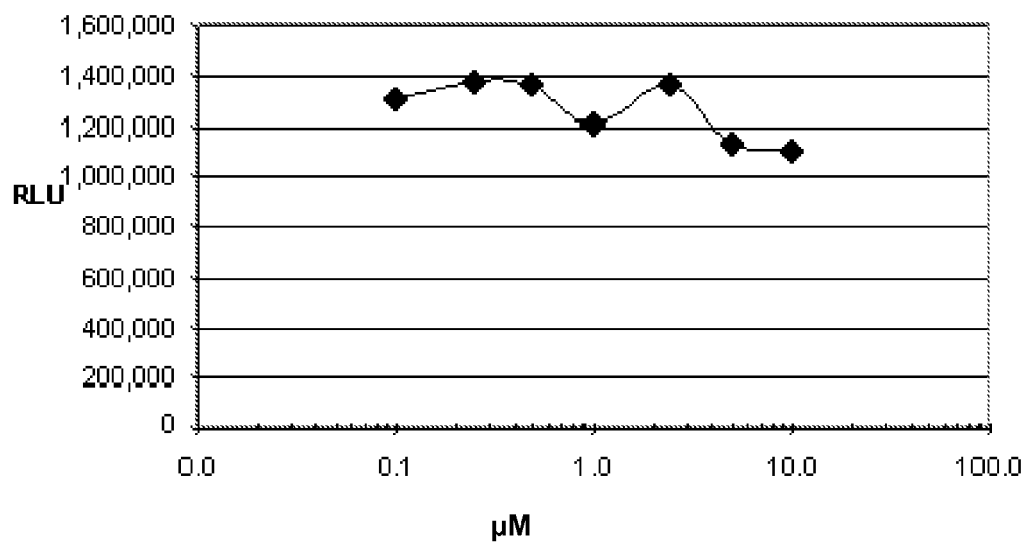
FIGS. 2A and 2B are graphs showing the activity of PARP in the presence of various concentrations of the hydrochloride salt of R-55 (PARP activity is represented as relative light units (RLU)
Figure 2B:
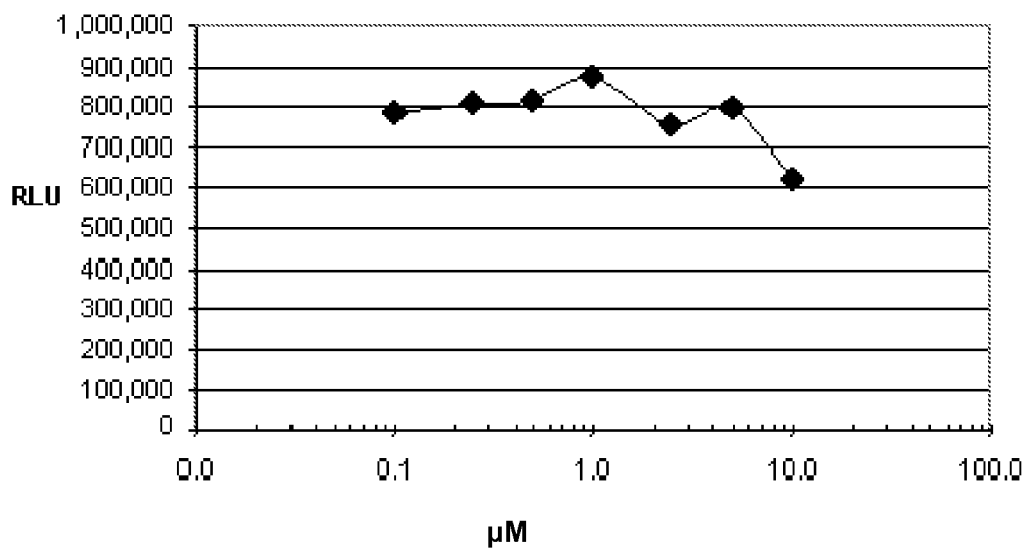
Figure 3A:
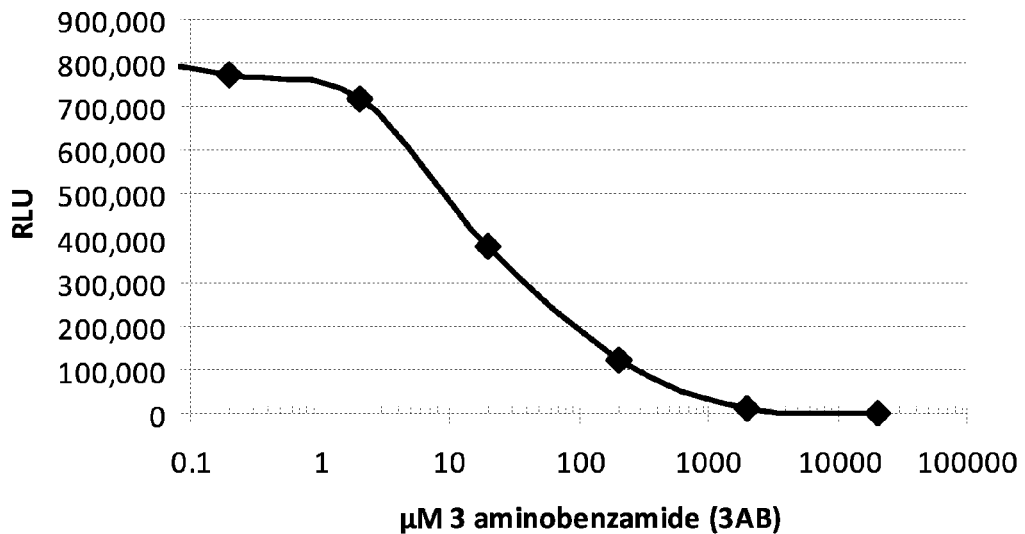
FIGS. 3A and 3B are graphs showing the activity of PARP in the presence of various concentrations of 3-aminobenzamide (3-AB), a weak PARP inhibitor (PARP activity is represented as relative light units (RLU)
Figure 3B:
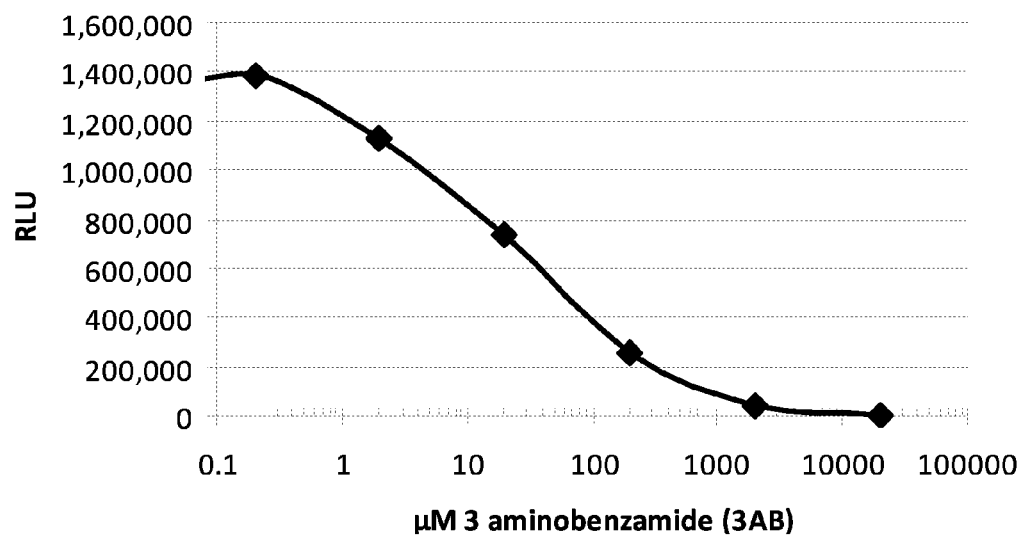

Similarly, as shown in FIGS. 2A and 2B, the hydrochloride salt of R-55 did not exhibit any significant inhibition of PARP in either Assay 1 (FIG. 2A) or Assay 2 (FIG. 2B). For comparison, FIGS. 3A and 3B show the inhibition of PARP by the 3-aminobenzamide (3-AB) control in Assay 1 (FIG. 3A) and Assay 2 (FIG. 3B).

The above results are summarized in Table 9 below.

TABLE 9

Inhibition of PARP-1 by 5 μM or 10 μM R-55, R-55 hydrochloride salt, and 3-AB (average results from two assays)

| Compound | % PARP-1 inhibition at 5 μM | % PARP-1 inhibition at 10 μM |
|---|---|---|
| 3-AB | 21 | 40 |
| R-55 | 19 | 21 |
| R-55 HCl salt | 10 | 21 |

The above results indicate that R-55 is relatively selective for $D_{4.4}$ receptor, and would consequently cause fewer, if any, significant side effects, compared to the other tested compounds.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

LIST OF REFERENCES CITED

Andersson, K. *Pharmacol. Rev.* 2001, 53, 417-450.
Beavo, J. A. *Physiol. Rev.* 1998, 75, 725.
Boyajian, C. L. & Leslie, F. M. *J. Pharmacol. Exp. Ther.* 1987, 241:1092-1098.
Broadhurst, A. M., et al. *Life Sci.* 1988, 43:83-92.
Brioni, J. D., et al. *P. Proc. Natl. Acad. Sci. U.S.A.* 2004, 101:6758-6763.
Dearry, A., et al. *Nature.* 1990, 347:72-76.
Enguehard-Gueiffier et al. *J Med Chem* 2006, 49:3938-3947
Evans L. E., et al. *Prog. Neuropsychopharmacol.* 1980, 4:293-302
Hayes, G., et al. *Mol. Endocrinol.* 1992, 6:920-926.
Hyttel, J. *Prog. Neuro-Psychopharmacol. Biol. Psychiat.* 1982, 6:277-95
Grandy, D. K., et al. *Proc. Natl. Acad. Sci. USA.* 1989, 86:9762-9766.
Greengrass, P., Bremner, R. *Eur. J. Pharmacol.* 1979, 55:323-326.
Gundlach, A. L., et al. *Life Sciences* 1984, 35:1981-1988
Jarvis, K. R., et al. *J. Receptor Research* 1973, 13(1-4): 573-590
Lewis, K., et al. *Proc. Natl. Acad. Sci. USA.* 2001, 98:7570-7575.
Martin, G. R. & Humphrey, P. P. A. *Neuropharmacol.* 1994, 33:261-273.
May, J. A., et al. *J. Pharmacol. Exp. Ther.* 2003, 306:301-309.
Melis, M. & Argiolas, A. *Neurosci. Biobehav. Rev.* 1995, 19:19-38.
Melis, M. R., et al. *Eur. J. Neurosci.* 2006, 24:2021-2030
Missale, C., et al. *Physiol. Rev.* 1998, 78, 189-225.
Moreland, R. B., et al. *Life Sci.* 1995, 62, PL309.
Moreland, R. B., et al. *Pharmacol. Biochem. Behav.* 2005, 82:140-147
Nakane, M., et al. *Neuropharmacology* 2005, 49:112-121
Schioth, H. B., et al. *Pharmacol. Toxicol.* 1996, 79:161-165.
Schioth, H. B., et al. *Peptides.* 1997, 18:1009-1013.
Sokoloff, P., et al. *Nature.* 1990, 347:146-151.
Sunahara, R. K., et al. *Nature.* 1991, 350:614-619.
Sutton, S. W., et al. *Endocrinology.* 1995, 136:1097-1102.
Terret, N. K., et al. *Bioorg. Med. Chem. Lett.* 1996, 6, 1819.
Van Tol H. H., et al. *Nature* 1991, 350:610-614
Van Tol H. H., et al. *Nature* 1992, 358: 149-152

Weinshank, R. L., et al. *J. Biol. Chem.* 1991, 266:22427-22435.
Wolf, W. A. & Schutz, J. S. *J. Neurochem.* 1997, 69:1449-1458.
Zhou, Q.-Y., et al. *Nature.* 1990, 347:76-80.

What is claimed is:

1. A compound having the general Formula I:

Formula I or a pharmaceutically acceptable salt thereof,
wherein:
Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted,
wherein at least one of $R_1$-$R_5$ has the general Formula II:

Formula II wherein:
A is selected from the group consisting of a carbon atom and S=O;
B is absent or is a substituted or non-substituted, saturated or non-saturated alkylene chain; and
D is selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted.

2. The compound of claim 1, wherein $R_1$ is said general Formula II.

3. The compound of claim 1, wherein A is a carbon atom.

4. The compound of claim 1, wherein D is a substituted or non-substituted aryl.

5. The compound of claim 1, wherein D is a cycloalkyl selected from the group consisting of cyclopropyl, cyclopentyl, cyclohexyl, adamantyl, and 3-oxo-4,7,7-trimethyl-2-oxabicyclo [2.2.1]heptanyl.

6. The compound of claim 1, wherein D is a non-substituted alkyl.

7. The compound of claim 4, wherein B is absent.

8. The compound of claim 4, wherein B is alkyl.

9. A pharmaceutical composition comprising the compound of claim 1 and a pharmaceutically acceptable carrier.

10. A method of treating a sexual disorder mediated by D4 dopamine receptor, the method comprising administering to a subject in need thereof a therapeutically effective amount of the compound of claim 1.

11. The method of claim 10, wherein said compound is administered transdermally.

12. The method of claim 10, wherein said subject is a female subject.

13. A pharmaceutical composition comprising a compound having the general Formula III:

Formula III or a pharmaceutically acceptable salt thereof,
wherein:
the dashed line denotes a saturated or non-saturated bond;
X is selected from the group consisting of CH, C and N, such that when X is C the dashed line denotes a non-saturated bond and when X is CIT or N the dashed line denotes a saturated bond;
Y is N or $CR_4$;
Z is N or $CR_5$; and
Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate sulfonyl sulfonamide, nitro, nitrile, isonitrile, thiirane, anticline, nitroso, hydrazine, sulfate, azide, phosphonyl, phosphinyl, urea, thiourea, carbamyl and thiocarbainyl, each being substituted or non-substituted,
wherein at least one of $R_1$-$R_5$ is selected from the group consisting of carboxy and sulfonate having the general Formula II:

Formula II wherein:
A is selected from the group consisting of a carbon atom and S=O;
B is absent or is a substituted or non-substituted, saturated or non-saturated alkylene chain; and D is selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, and a pharmaceutically acceptable e carrier, the composition being formulated for transdermal administration.

14. The pharmaceutical composition of claim 13, wherein $R_1$ is said general Formula II.

15. The pharmaceutical composition of claim 13, wherein said X is N.

16. The pharmaceutical composition of claim 13, wherein said Y is $CR_4$ and said Z is $CR_5$.

17. The pharmaceutical composition of claim 13, wherein a concentration of said compound is at least 10 mg per 1 gram of said carrier.

18. The pharmaceutical composition of claim 13, being in a form of an oil-in-water emulsion.

19. The pharmaceutical composition of claim 18, wherein a lipophilic phase of said emulsion comprises at least one solvent selected from the group consisting of propylene glycol, propylene glycol monolaurate, and propylene glycol laurate.

20. The pharmaceutical composition of claim 18, wherein said emulsion comprises from 60 to 97.5 weight percents of a lipophilic phase.

* * * * *